United States Patent
Riebel et al.

(10) Patent No.: US 6,284,710 B1
(45) Date of Patent: Sep. 4, 2001

(54) SUBSTITUTING 2-AMINO-4-ALKYLAMINO-1,3,5-TRIAZINE AS HERBICIDE

(75) Inventors: Hans-Jochem Riebel, Wuppertal; Stefan Lehr, Leverkusen; Uwe Stelzer, Burscheid, all of (DE); Yukiyoshi Watanabe, Oyama (JP); Markus Dollinger, Overland Park, KS (US); Peter Dahmen, Neuss (DE); Seishi Ito, Oyama (JP); Toshio Goto, Kokubunji-machi (JP); Akihiko Yanagi, Oyama (JP)

(73) Assignees: Bayer Aktiengesellschaft, Leverkusen (DE); Nihon Bayer Agrochem K.L., Tokyo (JP)

( * ) Notice: Subject to any disclaimer, the term of this patent is extended or adjusted under 35 U.S.C. 154(b) by 0 days.

(21) Appl. No.: 09/284,052
(22) PCT Filed: Sep. 29, 1997
(86) PCT No.: PCT/EP97/05320
§ 371 Date: Apr. 6, 1999
§ 102(e) Date: Apr. 6, 1999
(87) PCT Pub. No.: WO98/15539
PCT Pub. Date: Apr. 16, 1998

(30) Foreign Application Priority Data

Oct. 10, 1996 (DE) .............................. 196 41 693

(51) Int. Cl.⁷ ..................... C07D 251/52; C07D 251/18; A01N 43/68; A01N 43/70
(52) U.S. Cl. .................... 504/234; 544/206; 544/207; 544/208; 544/209
(58) Field of Search ........................... 504/234; 544/206, 544/207, 208, 209

(56) References Cited

U.S. PATENT DOCUMENTS

| | | | |
|---|---|---|---|
| 3,816,419 | 6/1974 | Cross et al. | 260/249.9 |
| 3,932,167 | 1/1976 | Cross et al. | 71/93 |
| 4,844,731 | 7/1989 | Takematsu et al. | 71/93 |
| 5,073,648 | 12/1991 | Hagishita et al. | 564/374 |
| 5,286,905 | 2/1994 | Nakamura et al. | 564/234 |
| 5,403,815 | 4/1995 | Nishii et al. | 504/230 |
| 5,728,876 | 3/1998 | Balkenhohl et al. | 564/136 |
| 5,739,328 | 4/1998 | Schafer et al. | 544/194 |

FOREIGN PATENT DOCUMENTS

| | | |
|---|---|---|
| 3426919 | 1/1986 | (DE) . |
| 4000610 | 7/1991 | (DE) . |
| 0 320 898 | 6/1989 | (EP) . |
| 0 191 496 | 10/1990 | (EP) . |
| 411153 | 2/1991 | (EP) . |
| WO 97/00254 | 1/1997 | (WO) . |
| WO 97/08156 | 3/1997 | (WO) . |

OTHER PUBLICATIONS

Tetrahedron: Asymmetry, vol. 5, No. 5, pp. 817–820, (month unavailable) 1994, Calmes et al, Asymmetric Supported Reactions: Synthesis of Chiral Amines.

Tetrahedron Letters, vol. 29, No. 2, pp. 223–224, (month unavailable) 1988, Sakito et al, Asymmetric Reduction of Oxime Ethers. Distinction of Anti and Syn Isomers Leading to Enantiomeric Amines.

Tetrahedron Letters, vol. 36, No. 22, pp. 3917–3920, (month unavailable) 1995, Willicms et al Asymmetric Imine Isomerisation in the Enantioselective Synthesis of Chiral Amines from Prochiral Ketones.

Primary Examiner—John M. Ford
(74) Attorney, Agent, or Firm—Joseph C. Gil; James R. Franks; Jackie Ann Zurcher

(57) ABSTRACT

The invention relates to novel substituted 2-amino-4-alkylamino-1,3,5-triazines of the formula (I)

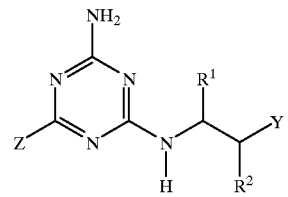

(I)

in which $R^1$ represents optionally substituted methyl,
$R^2$ represents hydrogen or alkyl,
Y represents in each case optionally substituted benzyl, naphthylmethyl, heterocyclylmethyl or heterocyclyloxy, and
Z represents hydrogen, represents halogen or represents in each case optionally substituted alkyl, alkoxy, alkylcarboxyl, alkoxycarbonyl, alkylthio, alkylsulphinyl, alkylsulphonyl, alkenyl or alkinyl, to processes and to novel intermediates for their preparation and to their use as herbicides.

4 Claims, No Drawings

SUBSTITUTING 2-AMINO-4-ALKYLAMINO-1,3,5-TRIAZINE AS HERBICIDE

This is a 371 of PCT/EP97/05320 filed Sep. 29, 1997

TECHNICAL FIELD OF THE INVENTION

The invention relates to novel substituted 2-amino-4-alkylamino-1,3,5-triazines, to a plurality of processes and to novel intermediates for their preparation and to their use as herbicides.

BACKGROUND OF THE INVENTION

A number of substituted 2,4-diamino-triazines is already known from the (patent) literature (cf. U.S. Pat. Nos. 3,816, 419, 3,932,167, EP 191496, EP 273328, EP 411153/WO 90/09378, WO 97/00254, WO 97/08156). However, these compounds have hitherto not attained any particular importance.

DETAILED DESCRIPTION OF THE INVENTION

This invention, accordingly, provides the novel substituted 2-amino-4-alkylamino-1,3,5-triazines of the general formula (I)

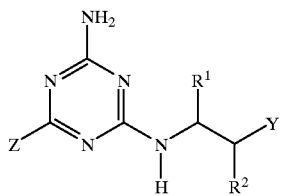

(I)

in which
$R^1$ represents optionally substituted methyl,
$R^2$ represents hydrogen or alkyl,
Y represents in each case optionally substituted benzyl, naphthylmethyl, heterocyclylmethyl or heterocyclyloxy, and
Z represents hydrogen, represents halogen or represents in each case optionally substituted alkyl, alkoxy, alkylcarbonyl, alkoxycarbonyl, alkylthio, alkylsulphinyl, alkylsulphonyl, alkenyl or alkinyl.

The novel 2-amino-4-alkylamino-1,3,5-triazines of the general formula (I) are obtained when
(a) substituted biguanides of the general formula (II),

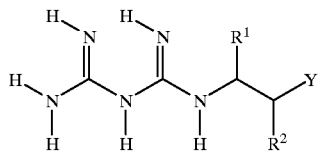

(II)

in which
$R^1$, $R^2$ and Y are each as defined above
—and/or acid adducts of compounds of the general formula (II)—are reacted with alkoxycarbonyl compounds of the general formula (III)

 (III)

in which

Z is as defined above and
R' represents alkyl,
if appropriate in the presence of a reaction auxiliary and if appropriate in the presence of a diluent,
or when
(b) substituted triazines of the general formula (IV)

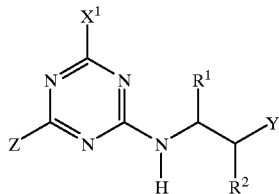

(IV)

in which
$R^1$, $R^2$, Y and Z are each as defined above and
$X^1$ represents halogen or alkoxy
are reacted with ammonia, if appropriate in the presence of a reaction auxiliary and if appropriate in the presence of a diluent,
or when
(c) substituted aminotriazines of the general formula (V),

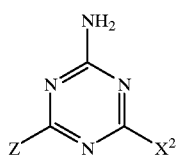

(V)

in which
Z is as defined above and
$X^2$ represents halogen or alkoxy
are reacted with substituted alkylamines of the general formula (VI),

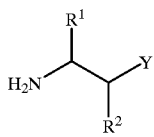

(VI)

in which
$R^1$, $R^2$ and Y are each as defined above,
if appropriate in the presence of a reaction auxiliary and if appropriate in the presence of a diluent,
and, if appropriate, further conversions within the scope of the above definition of substituents are carried out by customary methods on the compounds of the general formula (I) obtained by the processes described under (a), (b) or (c).

The novel substituted 2-amino-4-alkylamino-1,3,5-triazines of the general formula (I) have strong and selective herbicidal activity.

The compounds of the general formula (I) according to the invention contain at least one asymmetrically substituted carbon atom and can therefore be present in different enantiomeric (R- and S-configured forms) or diastereomeric forms. The invention relates both to the different possible individual enantiomeric or stereoisomeric forms of the compounds of the general formula (I), and to the mixtures of these isomeric compounds.

In the definitions, the hydrocarbon chains, such as alkyl—also in combination with heteroatoms, such as in alkoxy or alkylthio—are in each case straight-chain or branched.

Halogen generally represents fluorine, chlorine, bromine or iodine, preferably represents fluorine, chlorine or bromine, and in particular represents fluorine or chlorine.

The invention preferably provides compounds of the formula (I) in which $R^1$ represents optionally halogen-, cyano-, carboxyl-, carbamoyl-, thiocarbamoyl- or $C_1$–$C_4$-alkoxy-substituted methyl, $R^2$ represents hydrogen or alkyl having 1 to 3 carbon atoms, Y represents in each case optionally substituted benzyl, naphthylmethyl, heterocyclylmethyl or heterocyclyloxy, where the possible heterocyclyl groupings are preferably selected from the group below:

furyl, benzofuryl, dihydrobenzofuryl, tetrahydrofuryl, thienyl, benzothienyl, thiazolyl, benzothiazolyl, oxazolyl, benzoxazolyl, thiadiazolyl, oxadiazolyl, pyrazolyl, pyfrolyl, indolyl, pyridinyl, quinolinyl, isoquinolinyl and pyrimidinyl, and where the possible substituents are in each case preferably selected from the group below:

hydroxyl, cyano, nitro, halogen, in each case optionally hydroxyl-, cyano- or halogen-substituted alkyl or alkoxy having in each case 1 to 6 carbon atoms, in each case optionally halogen-substituted alkylcarbonyl, alkoxycarbonyl, alkylthio, alkylsulphinyl or alkylsulphonyl having in each case 1 to 6 carbon atoms in the alkyl groups, in each case optionally hydroxyl-, cyano-, nitro-, halogen-, $C_1$–$C_4$-alkyl, $C_1$–$C_4$-halogenoalkyl, $C_1$–$C_4$-alkoxy- or $C_1$–$C_4$-halogenoalkoxy-substituted phenyl or phenoxy, and also in each case optionally halogen-substituted methylenedioxy or ethylenedioxy, and Z represents hydrogen, represents halogen, represents in each case optionally hydroxyl-, cyano-, nitro-, halogen-, $C_1$–$C_4$-alkoxy-, $C_1$–C4-alkyl-carbonyl-, $C_1$–$C_4$-alkoxycarbonyl-, $C_1$–$C_4$-alkylthio-, $C_1$–$C_4$-alkylsulphinyl- or $C_1$–$C_4$-alkylsulphonyl-substituted alkyl, alkoxy, alkylcarbonyl, alkoxycarbonyl, alkylthio, alkylsulphinyl or alkylsulphonyl having in each case 1 to 6 carbon atoms in the alkyl groups, or represents optionally halogen-substituted alkenyl or alkinyl having in each case 2 to 6 carbon atoms.

From among the compounds of the formula (I) defined above as preferred ("preferably"), particular emphasis is given to the following groups:

(A) the compounds of the formula (I) in which $R^1$, $R^2$ and Z are each as defined above and Y represents in each case optionally substituted benzyl or naphthylmethyl, the possible substituents being as defined above;

(B) the compounds of the formula (I) in which $R^1$, $R^2$ and Z are each as defined above and Y represents in each case optionally substituted heterocyclylmethyl or heterocyclyloxy, the possible heterocyclyl groupings and the possible substituents being as defined above.

The invention in particular relates to compounds of the formula (I) in which $R^1$ represents optionally fluorine- and/or chlorine-substituted methyl, $R^2$ represents hydrogen, methyl or ethyl, Y represents in each case optionally substituted benzyl, naphthylmethyl, heterocyclylmethyl or heterocyclyloxy, where the possible heterocyclyl radicals are preferably selected from the group below:

furyl, benzofuryl, dihydrobenzofuryl, tetrahydrofuryl, thienyl, benzothienyl, thiazolyl, benzothiazolyl, oxazolyl, benzoxazolyl, thiadiazolyl, oxadiazolyl, pyrazolyl, pyrrolyl, indolyl, pyridinyl, quinolinyl, isoquinolinyl and pyrimidinyl, and where the possible substituents are in each case preferably selected from the group below:

hydroxyl, cyano, nitro, fluorine, chlorine, bromine, in each case optionally hydroxyl- cyano-, fluorine- or chlorine-substituted methyl, ethyl, n- or i-propyl, n-, i-, s- or t-butyl, methoxy, ethoxy, n- or i-propoxy, n-, i-, s- or t-butoxy, in each case optionally fluorine- or chlorine-substituted acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, in each case optionally hydroxyl-, cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl or phenoxy, and also in each case optionally fluorine- or chlorine-substituted methylenedioxy or ethylenedioxy, and Z represents hydrogen, represents fluorine, chlorine, bromine, represents in each case optionally hydroxyl-, cyano-. nitro-. fluorine-, chlorine-, methoxy-, ethoxy-, n- or i-propoxy-, n-, i-, s- or t-butoxy-, methylthio-ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents in each case optionally fluorine-, chlorine- or bromine-substituted ethenyl, propenyl, butenyl, ethinyl, propinyl or butinyl.

From among the compounds of the formula (I) defined above as being particularly preferred, particular emphasis is given to the following groups:

(AA) the compounds of the formula (I) in which $R^1$, $R^2$ and Z are each as defined above and Y represents in each case optionally substituted benzyl or naphthylmethyl, the possible substituents being as defined above, with the proviso that the substituents of the carbon atom to which $R^1$ is attached are arranged in the R configuration;

(BB) the compounds of the formula (I) in which $R^1$, $R^2$ and Z are each as defined above and Y represents in each case optionally substituted benzyl or naphthylmethyl, the possible substituents being as defined above, with the proviso that the substituents of the carbon atom to which $R^1$ is attached are arranged in the S configuration;

(CC) the compounds of the formula (I) in which $R^1$, $R^2$ and Z are each as defined above and Y represents in each case optionally substituted furylmethyl, thienylmethyl, pyridinylmethyl or pyrimidinylmethyl, the possible substituents being as defined above, with the proviso that these compounds are present as racemic mixtures;

(DD) the compounds of the formula (I) in which $R^1$, $R^2$ and Z are each as defined above and Y represents in each case optionally substituted furylmethyl, thienylmethyl, pyridinylmethyl or pyrimidinylmethyl, the possible substituents being as defined above, with the proviso that the substituents of the carbon atom to which R¹ is attached are arranged in the R configuration;

(EE) the compounds of the formula (I), in which R¹, R² and Z are each as defined above and Y represents in each case optionally substituted furylmethyl, thienylmethyl, pyridinylmethyl or pyrimidinylmethyl, the possible substituents being as defined above, with the proviso that the substituents of the carbon atom to which R¹ is attached are arranged in the S configuration;

The abovementioned general or preferred radical definitions apply both to the end products of the formula (I) and also, correspondingly, to the starting materials or intermediates required in each case for the preparation. These radical definitions can be combined with each other at will, i.e. including combinations between the abovementioned preferred ranges.

Examples of the compounds of the formula (I) according to the invention are listed in the groups below. The general formulae here represent in each case the R enantiomers, the S enantiomers and the racemates.

Group 1

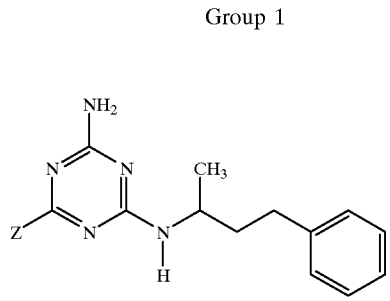

(I-1)

Here, Z has, for example, the meanings given below:

Hydrogen, methyl, ethyl, n- or i-propyl, n-, i-, s- or t-butyl, fluoromethyl, difluoromethyl, trifluoromethyl, chloromethyl, dichloromethyl, chlorofluoromethyl, chlorobromomethyl, chlorodifluoromethyl, fluorodichloromethyl, bromodifluoromethyl, trichloromethyl, 1-fluoro-ethyl, 2-fluoro-ethyl, 1-chloro-ethyl, 2-chloro-ethyl, 1-chloro-1-fluoro-ethyl, 1-fluoro-propyl, 2-fluoro-propyl, 3-fluoro-propyl, 1-fluoro-1-methyl-ethyl, 2-fluoro-1-methyl-ethyl, 1-chloro-1-methyl-ethyl, 1-fluoro-1-methyl-propyl, 1-chloro-1-ethyl-propyl, 1-fluoro-1-ethyl-propyl, 1-chloro-1-ethyl-propyl, 1-fluoro-2-methyl-propyl, 1-chloro-2-methyl-propyl, 1-chloro-propyl, 2-chloro-propyl, 3-chloro-propyl, 1-chloro-1-methyl-ethyl, 2-chloro-1-methyl-ethyl, 1,1-difluoro-ethyl, 1,2-difluoro-ethyl, 1,1-dichloro-ethyl, 2,2,2-trifluoro-ethyl, 1,2,2,2-tetrafluoro-ethyl, perfluoroethyl, 1,1-difluoro-propyl, 1,1-dichloro-propyl, perfluoropropyl, 1-fluoro-butyl, 1-chloro-butyl, perfluoropentyl, perfluorohexyl, 1-hydroxyl-ethyl, acetyl, 1,1-bis-acetyl-methyl, 1-acetyl-1-methoxycarbonyl-methyl, 1-acetyl-1-ethoxycarbonyl-methyl, methoxymethyl, 1,1-dimethoxy-methyl, 1-methoxy-ethyl, 2-methoxy-ethyl, 1,1-dimethoxy-ethyl, ethoxymethyl, 1-ethoxyethyl, 2-ethoxy-ethyl, 2-methoxy-1-methyl-ethyl, 2-methoxy-1-ethyl-ethyl, 2-ethoxy-1-methyl-ethyl, 2-ethoxy-1-ethyl-ethyl, methylthiomethyl, ethylthiomethyl, 1-methylthio-ethyl, 2-methylthioethyl, 1-ethylthio-ethyl, 2-ethylthioethyl, methylsulphinylmethyl, ethylsulphinylmethyl, methylsulphonylmethyl, ethylsulphonylmethyl, methoxy, ethoxy, n- or i- propoxy, methylthio, ethylthio, n- or i-propylthio, methylsulphinyl, ethylsulphinyl, methylsulphonyl, ethylsulphonyl, fluoromethoxy, difluoromethoxy, trifluoromethoxy, fluoroethoxy, difluoroethoxy, trifluoroethoxy, di fluoromethylthio, trifluoromethylthio, vinyl, 1-chloro-vinyl, 2-chloro-vinyl, 1-fluoro-vinyl, 2-fluoro-vinyl, 1-bromo-vinyl, 2-bromo-vinyl, 1,2-dichloro-vinyl, 1,2-dibromo-vinyl, 1,2-difluoro-vinyl, 2,2-dichloro-vinyl, 2,2-difluoro-vinyl, 2,2-dibromo-vinyl, 1-chloro-2-fluoro-vinyl, 2-bromo-2-chloro-vinyl, trichlorovinyl, allyl, 2-chloro-allyl, 3-chloro-allyl, 3,3-dichloro-allyl, 1-propenyl, isopropenyl, 1-chloro-2-propenyl, 1-fluoro-2-propenyl, 1-bromo-2-propenyl, 1,2-dichloro-1-propenyl, 1,2-dibromo-1-propenyl, 1,2-difluoro-1-propenyl, 1,1-dichloro-2-propenyl, 1,1-dibromo-2-propenyl, 1,1-difluoro-2-propenyl, 1,1,3,3,3-pentafluoro-2-propenyl, 2-buten-1-yl, 2-buten-2-yl, 3-chloro-2-butenyl, 3-bromo-2-butenyl, 3,3,3-trifluoro-2-butenyl, ethinyl, 2-chloro-ethinyl, 2-bromo-ethinyl, 1-propinyl, 2-propinyl, 3,3,3-trifluoro-1-propinyl.

Group 2

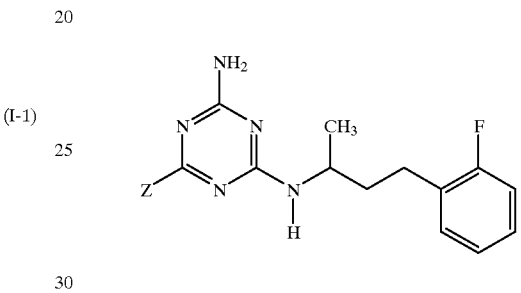

(I-2)

Here, Z has, for example, the meanings given above in group 1.

Group 3

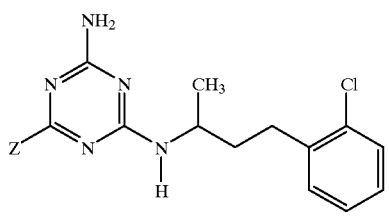

(I-3)

Here, Z has, for example, the meanings given above in group 1.

Group 4

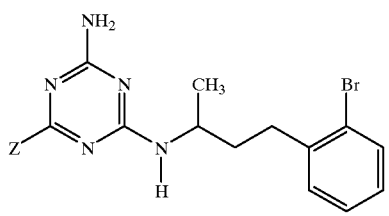

(I-4)

Here, Z has, for example, the meanings given above in group 1.

Group 5

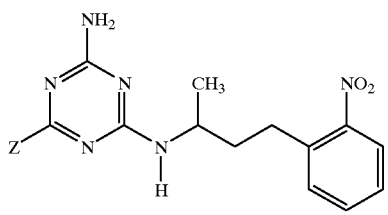
(I-5)

Here, Z has, for example, the meanings given above in group 1.

Group 6

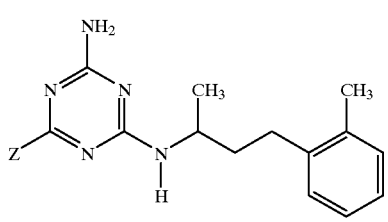
(I-6)

Here, Z has, for example, the meanings given above in group 1.

Group 7

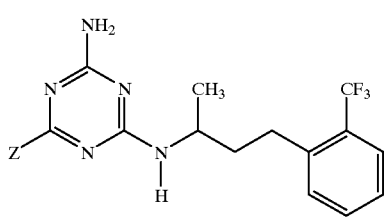
(I-7)

Here, Z has, for example. the meanings given in group 1.

Group 8

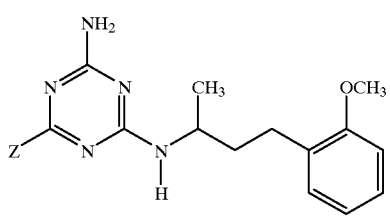
(I-8)

Here, Z has, for example. the meanings given in group 1.

Group 9

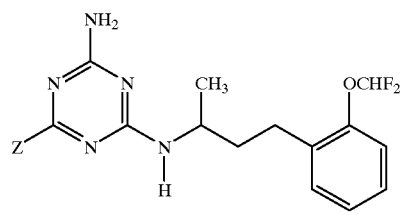
(I-9)

Here, Z has, for example. the meanings given in group 1.

Group 10

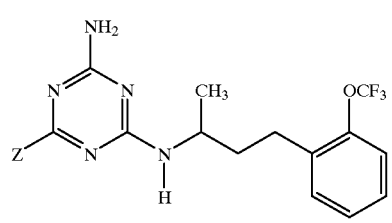
(I-10)

Here, Z has, for example. the meanings given in group 1.

Group 11

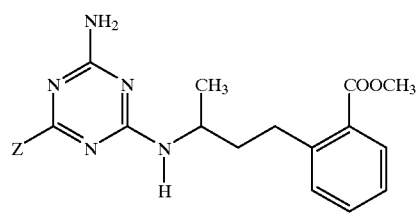
(I-11)

Here, Z has, for example. the meanings given in group 1.

Group 12

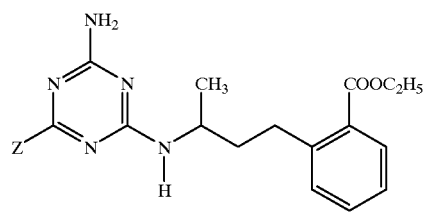
(I-12)

Here, Z has, for example. the meanings given in group 1.

Group 13

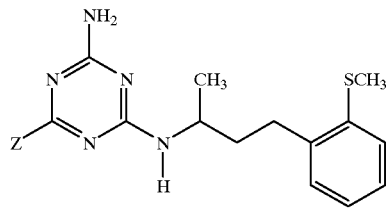
(I-13)

Here, Z has, for example. the meanings given in group 1.

Group 14

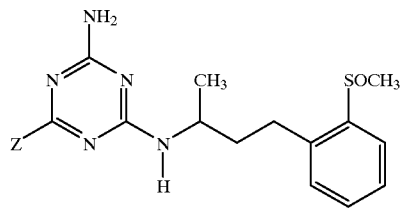
(I-14)

Here, Z has, for example. the meanings given in group 1.

Group 15

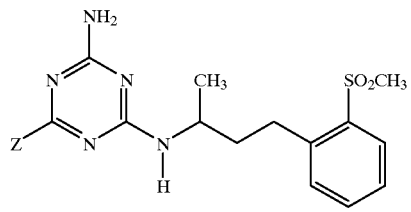
(I-15)

Here, Z has, for example. the meanings given in group 1.

Group 16

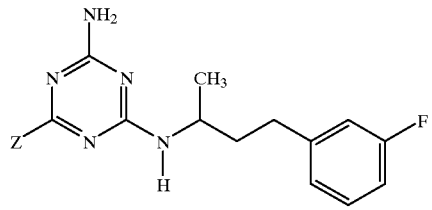
(I-16)

Here, Z has, for example, the meanings given above in group 1.

Group 17

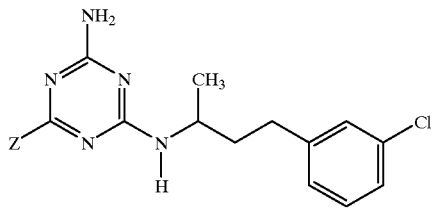
(I-17)

Here, Z has, for example, the meanings given above in group 1.

Group 18

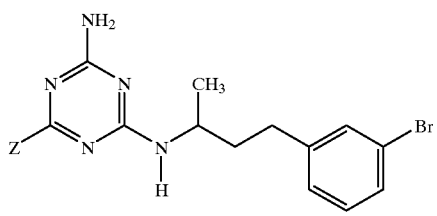
(I-18)

Here, Z has, for example, the meanings given above in group 1.

Group 19

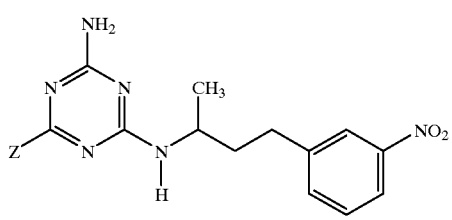
(I-19)

Here, Z has, for example, the meanings given above in group 1.

Group 20

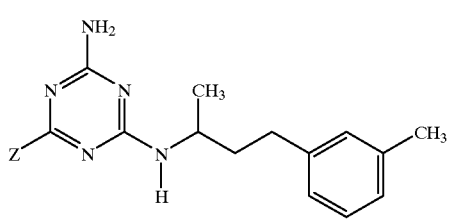
(I-20)

Here, Z has, for example, the meanings given above in group 1.

Group 21

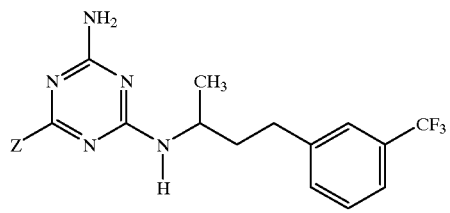
(I-21)

Here, Z has, for example, the meanings given above in group 1.

Group 22

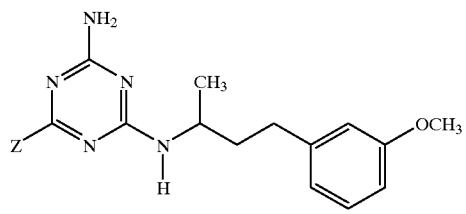
(I-22)

Here, Z has, for example, the meanings given above in group 1.

Group 23

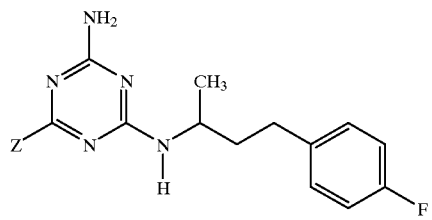
(I-23)

Here, Z has, for example, the meanings given above in group 1.

Group 24

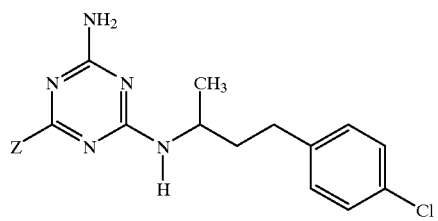
(I-24)

Here, Z has, for example, the meanings given above in group 1.

Group 25

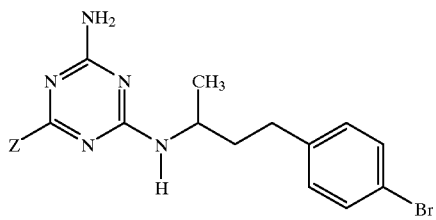
(I-25)

Here, Z has, for example, the meanings given above in group 1.

Group 26

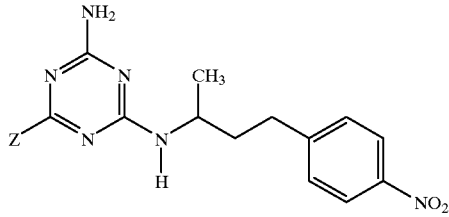
(I-26)

Here, Z has, for example, the meanings given above in group 1.

Group 27

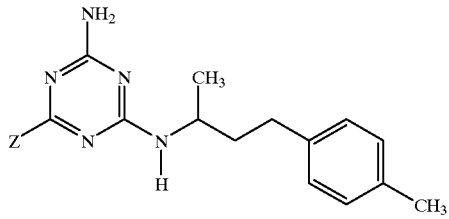
(I-27)

Here, Z has, for example, the meanings given above in group 1.

Group 28

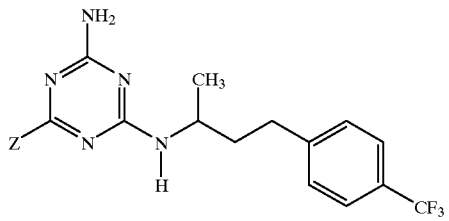
(I-28)

Here, Z has, for example, the meanings given above in group 1.

Group 29

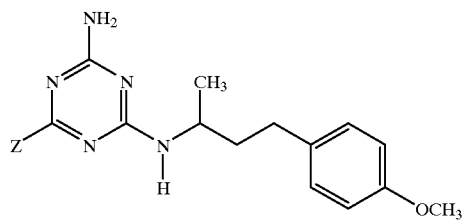
(I-29)

Here, Z has, for example, the meanings given above in group 1.

Group 30

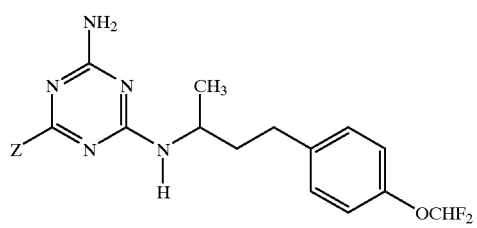
(I-30)

Here, Z has, for example, the meanings given above in group 1.

Group 31

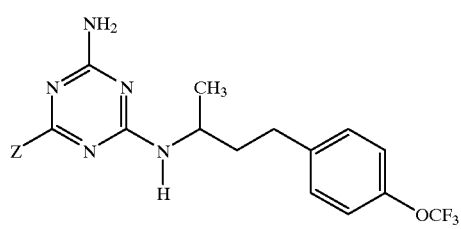
(I-31)

Here, Z has, for example, the meanings given above in group 1.

Group 32

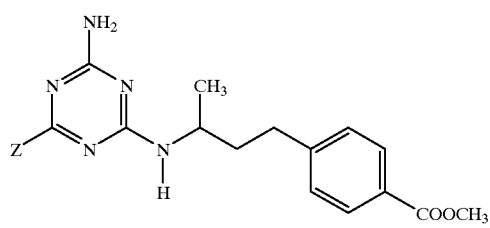
(I-32)

Here, Z has for example, the meanings given above in group 1.

Group 33

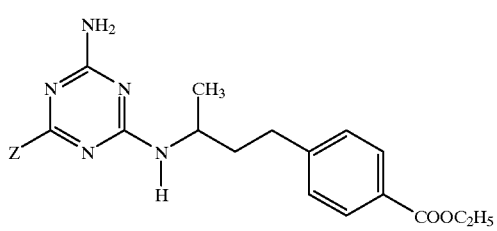
(I-33)

Here, Z has, for example, the meanings given above in group 1.

Group 34

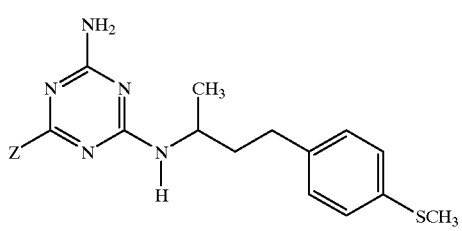
(I-34)

Here, Z has, for example, the meanings given above in group 1.

Group 35

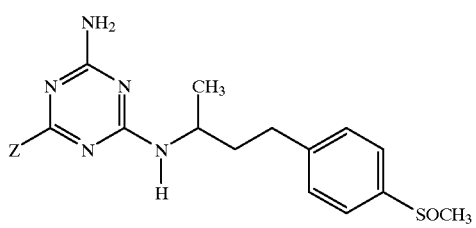
(I-35)

Here, Z has, for example, the meanings given above in group 1.

Group 36

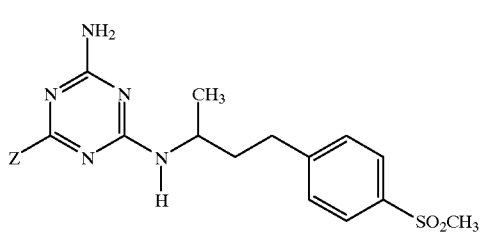
(I-36)

Here, Z has, for example, the meanings given above in group 1.

Group 37

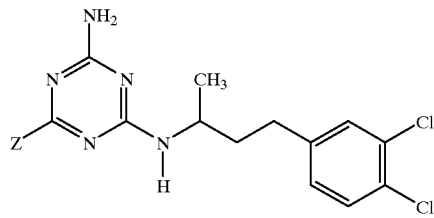
(I-37)

Here, Z has, for example, the meanings given above in group 1.

Group 38

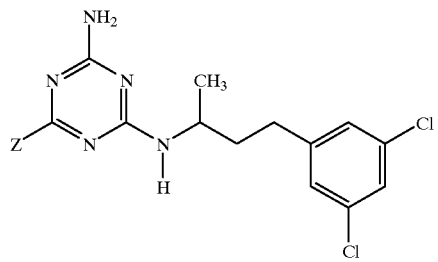
(I-38)

Here, Z has, for example, the meanings given above in group 1.

Group 39

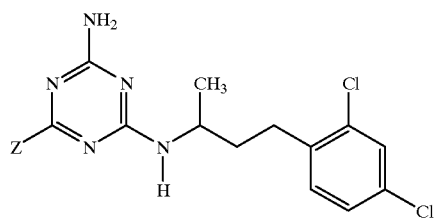
(I-39)

Here, Z has, for example, the meanings given above in group 1.

Group 40

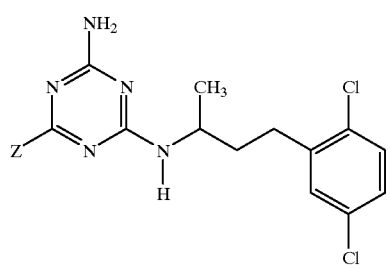
(I-40)

Here, Z has, for example, the meanings given above in group 1.

Group 41

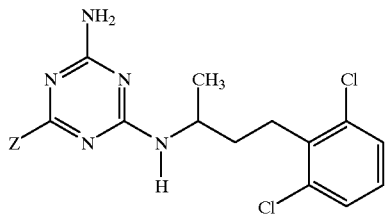
(I-41)

Here, Z has, for example, the meanings given above in group 1.

Group 42

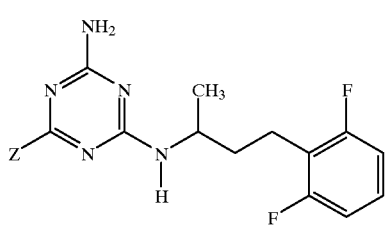
(I-42)

Here, Z has, for example, the meanings given above in group 1.

Group 43

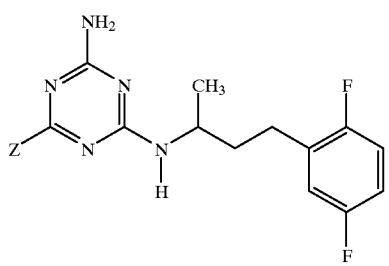
(I-43)

Here, Z has, for example, the meanings given above in group 1.

Group 44

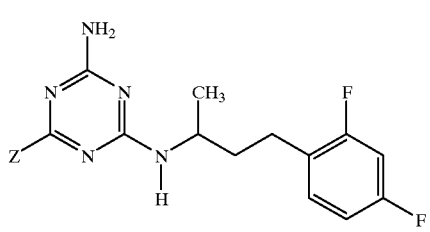
(I-44)

Here, Z has, for example, the meanings given above in group 1.

Group 45

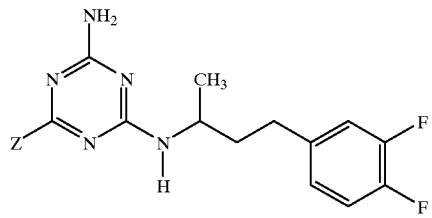
(I-45)

Here, Z has, for example, the meanings given above in group 1.

Group 46

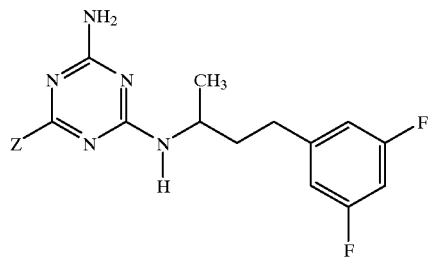
(I-46)

Here, Z has, for example, the meanings given above in group 1.

Group 47

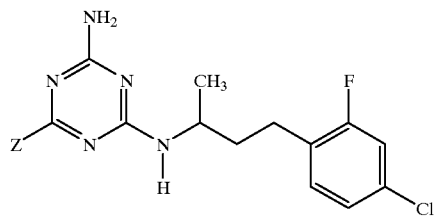
(I-47)

Here, Z has, for example, the meanings given above in group 1.

Group 48

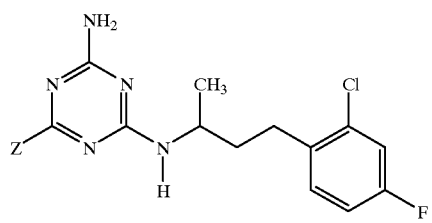
(I-48)

Here, Z has, for example, the meanings given above in group 1.

Group 49

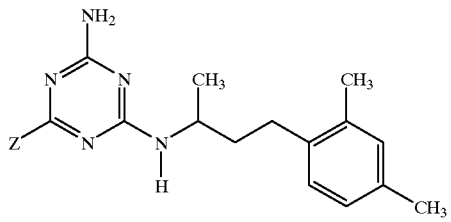
(I-49)

Here, Z has, for example, the meanings given above in group 1.

Group 50

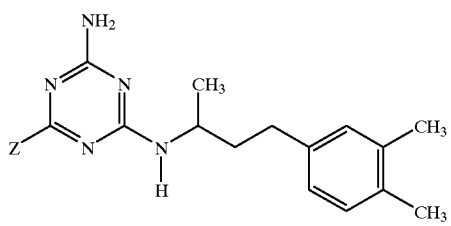
(I-50)

Here, Z has, for example, the meanings given above in group 1.

Group 51

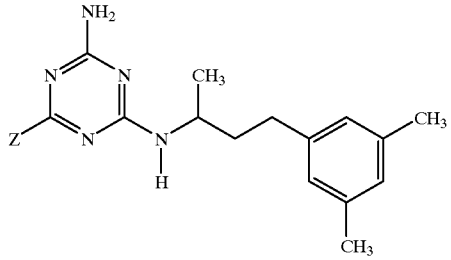
(I-51)

Here, Z has, for example, the meanings given above in group 1.

Group 52

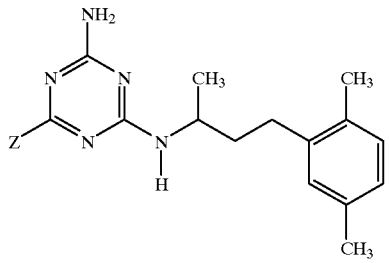
(I-52)

Here, Z has, for example, the meanings given above in group 1.

Group 53

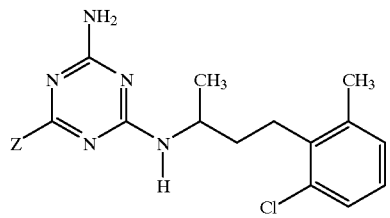
(I-53)

Here, Z has, for example, the meanings given above in group 1.

Group 54

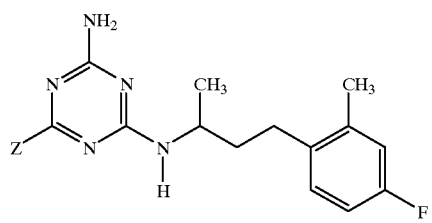
(I-54)

Here, Z has, for example, the meanings given above in group 1.

Group 55

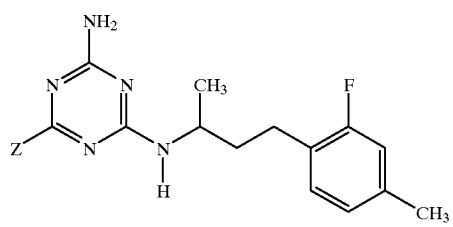
(I-55)

Here, Z has, for example, the meanings given above in group 1.

Group 56

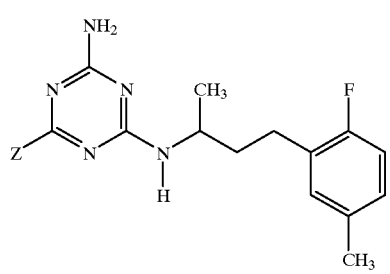
(I-56)

Here, Z has, for example, the meanings given above in group 1.

Group 57

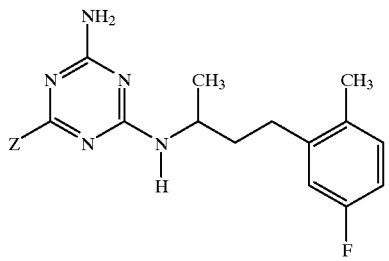
(I-57)

Here, Z has, for example, the meanings given above in group 1.

Group 58

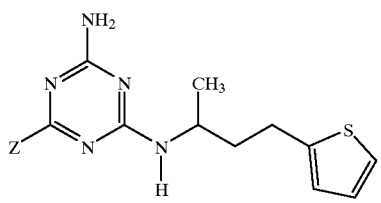
(I-58)

Here, Z has, for example, the meanings given above in group 1.

Group 59

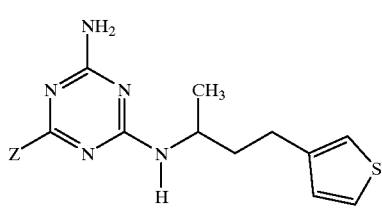
(I-59)

Here, Z has, for example, the meanings given above in group 1.

Group 60

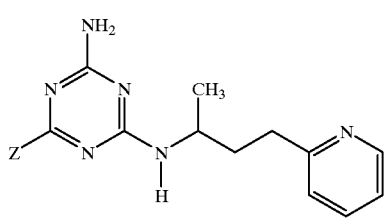
(I-60)

Here, Z has, for example, the meanings given above in group 1.

Group 61

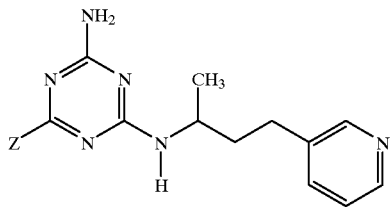
(I-61)

Here, Z has, for example, the meanings given above in group 1.

Group 62

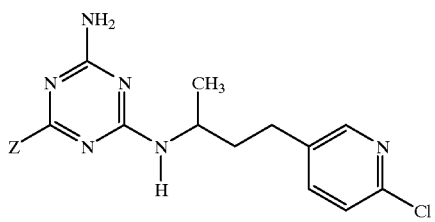
(I-62)

Here, Z has, for example, the meanings given above in group 1.

Group 63

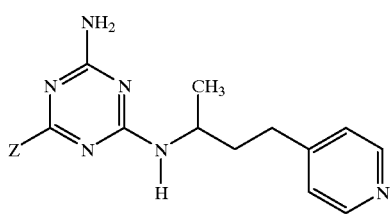
(I-63)

Here, Z has, for example, the meanings given above in group 1.

Group 64

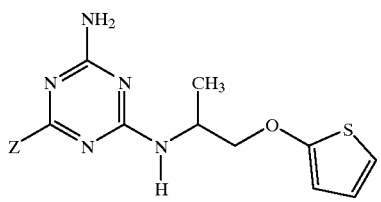
(I-64)

Here, Z has, for example, the meanings given above in group 1.

Group 65

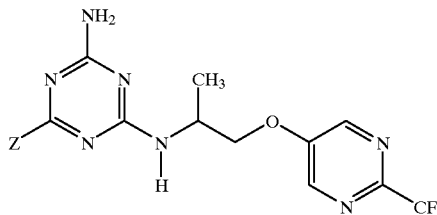
(I-65)

Here, Z has, for example, the meanings given above in group 1.

Group 66

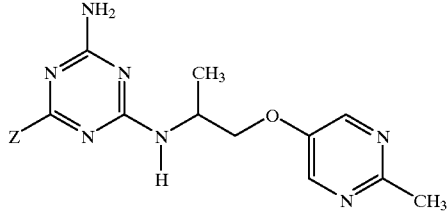
(I-66)

Here, Z has, for example, the meanings given above in group 1.

Group 67

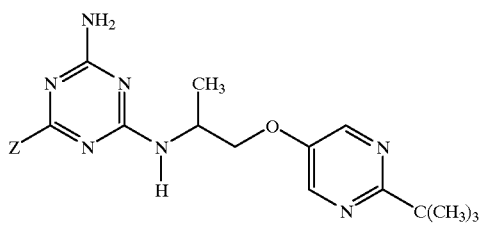
(I-67)

Here, Z has, for example, the meanings given above in group 1.

Group 68

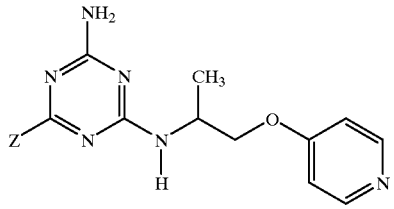
(I-68)

Here, Z has, for example, the meanings given above in group 1.

Group 69

(I-69)

Here, Z has, for example, the meanings given above in group 1.

Group 70

(I-70)

Here, Z has, for example, the meanings given above in group 1.

Group 71

(I-71)

Here, Z has, for example, the meanings given above in group 1.

Group 72

(I-72)

Here, Z has, for example, the meanings given above in group 1.

Group 73

(I-73)

Here, Z has, for example, the meanings given above in group 1.

Group 74

(I-74)

Here, Z has, for example, the meanings given above in group 1.

Group 75

(I-75)

Here, Z has, for example, the meanings given above in group 1.

Group 76

(I-76)

Here, Z has, for example, the meanings given above in group 1.

Using, for example, 1-(1-methyl-3-phenyl-propyl)-biguanide and methyl trifluoroacetate as starting materials, the course of the reaction in the process (a) according to the invention can be illustrated by the following equation:

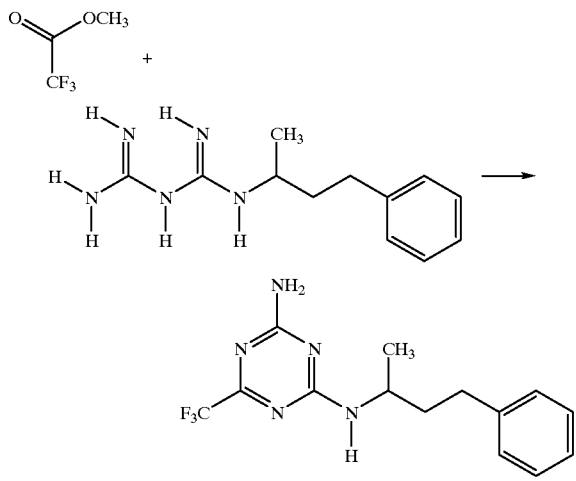

Using, for example, 2-chloro-4-(1-methyl-3-phenyl-propylamino)-6-trifluoromethyl-1,3,5-triazine and ammonia as starting materials, the course of the reaction in the process (b) according to the invention can be illustrated by the following equation:

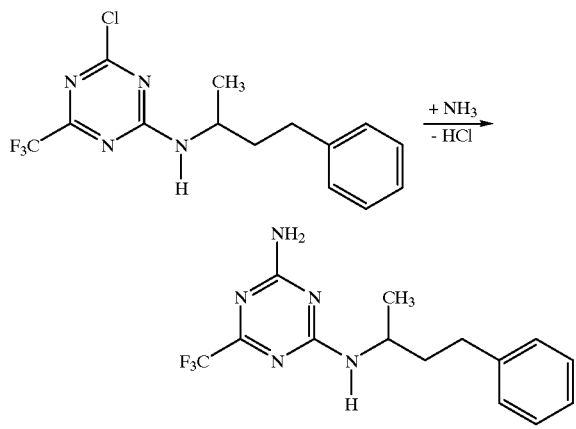

Using, for example, 2-amino-4-methoxy-6-trifluoromethyl-1,3,5-triazine and 3-phenyl-1-trifluoromethyl-propylamine as starting materials, the course of the reaction in the process (c) according to the invention can be illustrated by the following equation:

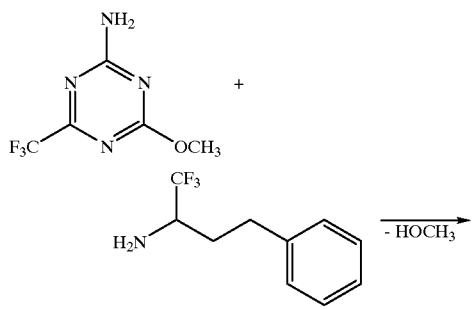

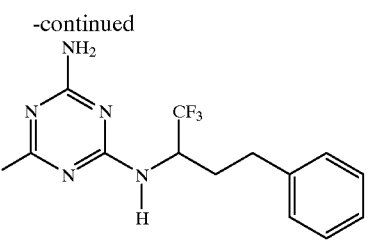

The formula (II) provides a general definition of the substituted biguanides to be used as starting materials in the process (a) according to the invention for preparing compounds of the formula (I). In the formula (II), $R^1$, $R^2$ and Y each preferably or in particular have those meanings which have already been mentioned above, in connection with the description of the compounds of the formula (I) according to the invention, as being preferred or as being particularly preferred for $R^1$, $R^2$ and Y.

Examples of the substituted biguanides of the formula (II) which may be mentioned are:

1-(1-methyl-3-phenyl-propyl)-, 1-(1,2-dimethyl-3-phenyl-propyl)-, 1-(1-methyl-3-(2-fluoro-phenyl)-propyl)-, 1-(1-methyl-3-(3-fluoro-phenyl)-propyl)-, 1-(1-methyl-3-(4-fluoro-phenyl)-propyl)-, 1-(1-methyl-3-(2-chloro-phenyl)-propyl)-, 1-(1-methyl-3-(3-chloro-phenyl)-propyl)-, 1-(1-methyl-3-(4-chloro-phenyl)-propyl)-, 1-(1-methyl-3-(2-bromo-phenyl)-propyl)-, 1-(1-methyl-3-(3-bromo-phenyl)-propyl)-, 1-(1-methyl-3-(4-bromo-phenyl)-propyl)-, 1-(1-methyl-3-(2-nitro-phenyl)-propyl)-, 1-(1-methyl-3-(3-nitro-phenyl)-propyl)-, 1-(1-methyl-3-(4-nitro-phenyl)-propyl)-, 1-(1-methyl-3-(2-methyl-phenyl)-propyl)-, 1-(1-methyl-3-(3-methyl-phenyl)-propyl)-, 1-(1-methyl-3-(4-methyl-phenyl)-propyl)-, 1-(1-methyl-3-(2-trifluoromethyl-phenyl)-propyl)-, 1-(1-methyl-3-(3-trifluoromethyl-phenyl)-propyl)-, 1-(1-methyl-3-(4-trifluoromethyl-phenyl)-propyl)-, 1-(1-methyl-3-(2-methoxy-phenyl)-propyl)-, 1-(1-methyl-3-(3-methoxy-phenyl)-propyl)-, 1-(1-methyl-3-(4-methoxy-phenyl)-propyl)-, 1-(1-methyl-3-(2-difluoromethoxy-phenyl)-propyl)-, 1-(1-methyl-3-(2-difluoromethoxy-phenyl)-propyl)-, 1-(1-methyl-3-(2-difluoromethoxy-phenyl)-propyl)-, 1-(1-methyl-3-(2-trifluoromethoxy-phenyl)-propyl)-, 1-(1-methyl-3-(3-trifluoromethoxy-phenyl)-propyl), 1-(1-methyl-3-(4-trifluoromethoxy-phenyl)-propyl)-, 1-(1-methyl-3-(2-methoxycarbonyl-phenyl)-propyl)-, 1-(1-methyl-3-(2-ethoxycarbonyl-phenyl)-propyl)-, 1-(1-methyl-3-(4-methoxycarbonyl-phenyl)-propyl)-, 1-(1-methyl-3-(4-ethoxycarbonyl-phenyl)-propyl)-, 1-(1-methyl-3-(2-methylthio-phenyl)-propyl)-, 1-(1-methyl-3-(4-methylthio-phenyl)-propyl)-, 1-(1-methyl-3-(2-methylsulphinyl-phenyl)-propyl)-, 1-(1-methyl-3-(4-methylsulphinyl-phenyl)-propyl)-, 1-(1-methyl-3-(2-methylsulphonyl-phenyl)-propyl)-, 1-(1-methyl-3-(4-methylsulphonyl-phenyl)-propyl)-, 1-(1-methyl-3-(3,4-dichloro-phenyl)-propyl)-, 1-(1-methyl-3-(2,4-dichloro-phenyl)-propyl)-, 1-(1-methyl-3-(2,5-dichloro-phenyl)-propyl)-, 1-(1-methyl-3-(2,6-dichloro-phenyl)-propyl)-, 1-(1-methyl-3-(2,6-difluoro-phenyl)-propyl)-, 1-(1-methyl-3-(2,5-difluoro-phenyl)-propyl)-, 1-(1-methyl-3-(2,4-difluoro-phenyl)-propyl)-, 1-(1-methyl-3-(3,4-difluoro-phenyl)-propyl)-, 1-(1-methyl-3-(3,5-difluoro-phenyl)-propyl)-, 1-(1-methyl-3-(2-fluoro-4-chloro-phenyl)-propyl)-, 1-(1-methyl-3-(4-fluoro-2-chloro-phenyl)-propyl)-, 1-(1-methyl-3-(2,4-dimethyl-phenyl)-propyl)-, 1-(1-methyl-3-(3,4-dimethyl-phenyl)-propyl)-, 1-(1-methyl- 3-(3,5-dimethyl-phenyl)-propyl)-, 1-(1-methyl-3-(2,5-dimethyl-phenyl)-propyl)-, 1-(1-methyl-3-(2-chloro-6-methyl-phenyl)-propyl)-, 1-(1-methyl-3-(4-fluoro-2-methyl-phenyl)-propyl)-, 1-(1-methyl-3-(2-fluoro-4-methyl-phenyl)-propyl)-, 1-(1-methyl-3-(2-fluoro-5-methyl-phenyl)-propyl)-, 1-(1-methyl-3-(5-fluoro-2-methyl-phenyl)-propyl)-, 1-(1-methyl-3-thien-2-yl-propyl)-, 1-(1-methyl-3-thien-3-yl-propyl)-, 1-(1-methyl-3-pyridin-2-yl-propyl)-, 1-(1-methyl-3-pyridin-3yl-propyl)- and 1-(1-methyl-3-pyridin-4-yl-propyl)-biguanide.

Suitable acid adducts of compounds of the formula (II) are their addition products with protic acids, such as, for example with hydrogen chloride, hydrogen bromide, sulphuric acid, methanesulphonic acid, benzenesulphonic acid and p-toluenesulphonic acid.

The starting materials of the general formula (II) have hitherto not been disclosed in the literature; as novel substances, they also form part of the subject matter of the present application.

The novel substituted biguanides of the general formula (II) are obtained when substituted alkylamino compounds of the general formula (VI),

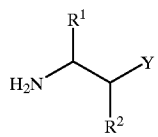

(VI)

in which
$R^1$, $R^2$ and Y are each as defined above
—and/or acid adducts of compounds of the general formula (V), such as, for example, the hydrochlorides—
are reacted with cyanoguanidine ("dicyanodiamide") of the formula (VII)

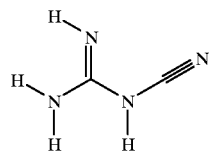

(VII)

if appropriate in the presence of a reaction auxiliary, such as, for example, hydrogen chloride, and if appropriate in the presence of a diluent, such as, for example, n-decane or 1,2-dichloro-benzene, at temperatures between 100° C. and 200° C. (cf. EP 492615, Preparation Examples).

The substituted alkylamino compounds of the general formula (VI) required as precursors for this purpose are known and/or can be prepared by processes known per se (cf. DE 3426919; DE 4000610; DE 4332738, EP 320898; EP 443606; Tetrahedron: Asymmetry 5 (1994), 817–820; Tetrahedron Lett. 29 (1988), 223–224; loc. cit. 36 (1995), 3917–3920; Preparation Examples).

The formula (III) provides a general definition of the alkoxycarbonyl compounds further to be used as starting materials in the process (a) according to the invention for preparing compounds of the formula (I). In the formula (III), Z preferably or in particular has that meaning which has already been mentioned above, in connection with the description of the compounds of the formula (I) according to the invention, as being preferred or as being particularly preferred for Z; R' preferably represents alkyl having 1 to 4 carbon atoms, and in particular represents methyl or ethyl.

The starting materials of the formula (III) are known chemicals for synthesis.

The formula (IV) provides a general definition of the substituted triazines to be used as starting materials in the process (b) according to the invention for preparing compounds of the formula (I). In the formula (IV), $R^1$, $R^2$, Y and Z each preferably or in particular have those meanings which have already been mentioned above, in connection with the description of the compounds of the formula (I) according to the invention, as being preferred or as being particularly preferred for $R^1$, $R^2$, Y and Z; $X^1$ preferably represents fluorine, chlorine, bromine, methoxy or ethoxy, and in particular represents chlorine.

Examples of the substituted triazines of the formula (IV) which may be mentioned are:

2-(1-methyl-3-phenyl-propylamino)-, 2-(1,2-dimethyl-3-phenyl-propylamino)-, 2-(1-methyl-3-(2-fluoro-phenyl)-propylamino)-, 2-(1-methyl-3-(3-fluoro-phenyl)-propylamino)-, 2-(1-methyl-3-(4-fluoro-phenyl)-propylamino)-, 2-(1-methyl-3-(2-chloro-phenyl)-propylamino)-, 2-(1-methyl-3-(3-chloro-phenyl)-propylamino)-, 2-(1-methyl-3-(4-chloro-phenyl)-propylamino)-, 2-(1-methyl-3-(2-bromo-phenyl)-propylamino)-, 2-(1-methyl-3-(3-bromo-phenyl)-propylamino)-, 2-(1-methyl-3-(4-bromo-phenyl)-propylamino)-, 2-(1-methyl-3-(2-nitro-phenyl)-propylamino)-, 2-(1-methyl-3-(3-nitro-phenyl)-propylamino)-, 2-(1-methyl-3-(4-nitro-phenyl)-propylamino)-, 2-(1-methyl-3-(2-methyl-phenyl)-propylamino)-, 2-(1-methyl-3-(3-methyl-phenyl)-propylamino)-, 2-(1-methyl-3-(4-methyl-phenyl)-propylamino)-, 2-(1-methyl-3-(2-trifluoromethyl-phenyl)-propylamino)-, 2-(1-methyl-3-(3-trifluoromethyl-phenyl)-propylamino)-, 2-(1-methyl-3-(4-trifluoromethyl-phenyl)-propylamino)-, 2-(1-methyl-3-(2-methoxy-phenyl)-propylamino)-, 2-(1-methyl-3-(3-methoxy-phenyl)-propylamino)-, 2-(1-methyl-3-(4-methoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-trifluoromethoxy-phenyl)-propylamino)-, 1-(1-methyl-3-(3-trifluoromethoxy-phenyl)-propylamino)-, 2-(1-methyl-3-(4-trifluoromethoxy-phenyl)-propylamino)-, 2-(1-methyl-3-(2-methoxycarbonyl-phenyl)-propylamino)-, 2-(1-methyl-3-(2-ethoxycarbonyl-phenyl)-propylamino)-, 2-(1-methyl-3-(4-methoxycarbonyl-phenyl)-propylamino)-, 2-(1-methyl-3-(4-ethoxycarbonyl-phenyl)-propylamino)-, 2-(1-methyl-3-(2-methylthio-phenyl)-propylamino)-, 2-(1-methyl-3-(4-methylthio-phenyl)-propylamino)-, 2-(1-methyl-3-(2-methylsulphinyl-phenyl)-propylamino)-, 2-(1-methyl-3-(4-methylsulphinyl-phenyl)-propylamino)-, 2-(1-methyl-3-(2-methylsulphonyl-phenyl)-propylamino)-, 2-(1-methyl-3-(4-methylsulphonyl-phenyl)-propylamino)-, 2-(1-methyl-3-(3,4-dichloro-phenyl)-propylamino)-, 2-(1-methyl-3-(2,4-dichloro-phenyl)-propylamino)-, 2-(1-methyl-3-(2,5-dichloro-phenyl)-propylamino)-, 2-(1-methyl-3-(2,6-dichloro-phenyl)-propylamino)-, 2-(1-methyl-3-(2,6-difluoro-phenyl)-propylamino)-, 2-(1-methyl-3-(2,5-difluoro-phenyl)-propylamino)-, 2-(1-methyl-3-(2,4-difluoro-phenyl)-propylamino)-, 2-(1-methyl-3-(3,4-difluoro-phenyl)-propylamino)-, 2-(1-methyl-3-(3,5-difluoro-phenyl)-propylamino)-, 2-(1-methyl-3-(2-fluoro-4-chloro-phenyl)-propylamino)-, 2-(1-methyl-3-(4-fluoro-2-chloro-phenyl)-propylamino)-, 2-(1-methyl-3-(2,4-dimethyl-phenyl)-propylamino)-, 2-(1-methyl-3-(3,4-dimethyl-phenyl)-propylamino)-, 2-(1-methyl-3-(3,5- dimethyl-phenyl)-propylamino)-, 2-(1-methyl-3-(2,5-dimethyl-phenyl)-propylamino)-, 2-(1-methyl-3-(2-chloro-6-methyl-phenyl)-propylamino)-, 2-(1-methyl-3-(4-fluoro-2-methyl-phenyl)-propylamino)-, 2-(1-methyl-3-(2-fluoro-4-methyl-phenyl)-propylamino)-, 2-(1-methyl-3-(2-fluoro-5-methyl-phenyl)-propylamino)-, 2-(1-methyl-3-(5-fluoro-2-methyl-phenyl)-propylamino)-, 2-(1-methyl-3-thien-2-yl-propylamino)-, 2-(1-methyl-3-thien-3-yl-propylamino)-, 2-(1-methyl-3-pyridin-2-yl-propylamino)-, 2-(1-methyl-3-pyridin-3-yl-propylamino)- and 2-(1-methyl-3-pyridin-4-yl-propylamino)- -4,6-dichloro-1,3,5-triazine;

2-(1-methyl-3-phenyl-propylamino)-, 2-(1,2-dimethyl-3-phenyl-propylaamino)-, 2-(1-methyl-3-(2-fluoro-phenyl)-propylamino)-, 2-(1-methyl-3-(3-fluoro-phenyl)-propylamino)-, 2-(1-methyl-3-(4-fluoro-phenyl)-propylamino)-, 2-(1-methyl-3-(2-chloro-phenyl)-propylamino)-, 2-(1-methyl-3-(3-chloro-phenyl)-propylamino)-, 2-(1-methyl-3-(4-chloro-phenyl)-propylamino)-, 2-(1-methyl-3-(2-bromo-phenyl)-propylamino)-,2-(1-methyl-3-(3-bromo-phenyl)-propylamino)-, 2-(1-methyl-3-(4-bromo-phenyl)-propylamino)-, 2-(1-methyl-3-(2-nitro-phenyl)-propylamino)-, 2-(1-methyl-3-(3-nitro-phenyl)-propylamino)-, 2-(1-methyl-3-(4-nitro-phenyl)-propylamino)-, 2-(1-methyl-3-(2-methyl-phenyl)-propylamino)-, 2-(1-methyl-3-(3-methyl-phenyl)-propylamino)-, 2-(1-methyl-3-(4-methyl-phenyl)-propylamino)-, 2-(1-methyl-3-(2-trifluoromethyl-phenyl)-propylamino)-, 2-(1-methyl-3-(3-trifluoromethyl-phenyl)-propylamino)-, 2-(1-methyl-3-(4-trifluoromethyl-phenyl)-propylamino)-, 2-(1-methyl-3-(2-methoxy-phenyl)-propylamino)-, 2-(1-methyl-3-(3-methoxy-phenyl)-propylamino)-, 2-(1-methyl-3-(4-methoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-trifluoromethoxy-phenyl)-propylamino)-, 1-(1-methyl-3-(3-trifluoromethoxy-phenyl)-propylamino)-, 2-(1-methyl-3-(4-trifluoromethoxy-phenyl)-propylamino)-, 2-(1-methyl-3-(2-methoxycarbonyl-phenyl)-propylamino)-, 2-(1-methyl-3-(2-ethoxycarbonyl-phenyl)-propylamino)-, 2-(1-methyl-3-(4-methoxycarbonyl-phenyl)-propylamino)-, 2-(1-methyl-3-(4-ethoxycarbonyl-phenyl)-propylamino)-, 2-(1-methyl-3-(2-methylthio-phenyl)-propylamino)-, 2-(1-methyl-3-(4-methylthio-phenyl)-propylamino)-, 2-(1-methyl-3-(2-methylsulphinyl-phenyl)-propylamino)-, 2-(1-methyl-3-(4-methylsulphinyl-phenyl)-propylamino)-, 2-(1-methyl-3-(2-methylsulphonyl-phenyl)-propylamino)-, 2-(1-methyl-3-(4-methylsulphonyl-phenyl)-propylamino)-, 2-(1-methyl-3-(3,4-dichloro-phenyl)-propylamino)-, 2-(1-methyl-3-(2,4-dichloro-phenyl)-propylamino)-, 2-(1-methyl-3-(2,5-dichloro-phenyl)-propylamino)-, 2-(1-methyl-3-(2,6-dichloro-phenyl)-propylamino)-, 2-(1-methyl-3-(2,6-difluoro-phenyl)-propylamino)-, 2-(1-methyl-3-(2,5-difluoro-phenyl)-propylamino)-, 2-(1-methyl-3-(2,4-difluoro-phenyl)-propylamino)-, 2-(1-methyl-3-(3,4-difluoro-phenyl)-propylamino)-, 2-(1-methyl-3-(3,5-difluoro-phenyl)-propylamino)-, 2-(1-methyl-3-(2-fluoro-4-chloro-phenyl)-propylamino)-, 2-(1-methyl-3-(4-fluoro-2-chloro-phenyl)-propylamino)-, 2 -(1-methyl-3-(2,4-dimethyl-phenyl)-propylamino)-, 2-(1-methyl-3-(3,4-dimethyl-phenyl)-propylamino)-, 2-(1-methyl-3-(3,5-dimethyl-phenyl)-propylamino)-, 2-(1-methyl-3-(2,5-dimethyl-phenyl)-propylamino)-, 2-(1-methyl-3-(2-chloro-6-methyl-phenyl)-propylamino)-, 2-(1-methyl-3-(4-fluoro-2-methyl-phenyl)-propylamino)-, 2-(1-methyl-3-(2-fluoro-4-methyl-phenyl)-propylamino)-, 2-(1-methyl-3-(2-fluoro-5-methyl-phenyl)-propylamino)-, 2-(1-methyl-3-(5-fluoro-2-methyl-phenyl)-propylamino)-, 2-(1-methyl-3-thien-2-yl-propylamino)-, 2-(1-methyl-3-thien-3-yl-propylamino)-, 2-(1-methyl-3-pyridin-2-yl-propylamino)-, 2-(1-methyl-3-pyridin-3-yl-propylamino)- and 2-(1-methyl-3-pyridin-4-yl-propylamino)- -4-chloro-6-methyl-1,3,5-triazine;

2-(1-methyl-3-phenyl-propylamino)-, 2-(1,2-dimethyl-3-phenyl-propylamino)-, 2-(1-methyl-3-(2-fluoro-phenyl)-propylamino)-, 2-(1-methyl-3-(3-fluoro-phenyl)-propylamino)-, 2-(1-methyl-3-(4-fluoro-phenyl)-propylamino)-, 2-(1-methyl-3-(2-chloro-phenyl)-propylamino)-, 2-(1-methyl-3-(3-chloro-phenyl)-propylamino)-, 2-(1-methyl-3-(4-chloro-phenyl)-propylamino)-, 2-(1-methyl-3-(2-bromo-phenyl)-propylamino)-, 2-(1-methyl-3-(3-bromo-phenyl)-propylamino)-, 2-(1-methyl-3-(4-bromo-phenyl)-propylamino)-, 2-(1-methyl-3-(2-nitro-phenyl)-propylamino)-, 2-(1-methyl-3-(3-nitro-phenyl)-propylamino)-, 2-(1-methyl-3-(4-nitro-phenyl)-propylamino)-, 2-(1-methyl-3-(2-methyl-phenyl)-propylamino)-, 2-(1-methyl-3-(3-methyl-phenyl)-propylamino)-, 2-(1-methyl-3-(4-methyl-phenyl)-propylamino)-, 2-(1-methyl-3-(2-trifluoromethyl-phenyl)-propylamino)-, 2-(1-methyl-3-(3-trifluoromethyl-phenyl)-propylamino)-, 2-(1-methyl-3-(4-trifluoromethyl-phenyl)-propylamino)-, 2-(1-methyl-3-(2-methoxy-phenyl)-propylamino)-, 2-(1-methyl-3-(3-methoxy-phenyl)-propylamino)-, 2-(1-methyl-3-(4-methoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-trifluoromethoxy-phenyl)-propylamino)-, 1-(1-methyl-3-(3-trifluoromethoxy-phenyl)-propylamino)-, 2-(1-methyl-3-(4-trifluoromethoxy-phenyl)-propylamino)-, 2-(1-methyl-3-(2-methoxycarbonyl-phenyl)-propylamino)-, 2-(1-methyl-3-(2-ethoxycarbonyl-phenyl)-propylamino)-, 2-(1-methyl-3-(4-methoxycarbonyl-phenyl)-propylamino)-, 2-(1-methyl-3-(4-ethoxycarbonyl-phenyl)-propylamino)-, 2-(1-methyl-3-(2 -methylthio-phenyl)-propylamino)-, 2-(1-methyl-3-(4-methylthio-phenyl)-propylamino)-, 2-(1-methyl-3-(2-methylsulphinyl-phenyl)-propylamino)-, 2-(1-methyl-3-(4-methylsulphinyl-phenyl)-propylamino)-, 2-(1-methyl-3-(2-methylsulphonyl-phenyl)-propylamino)-, 2-(1-methyl-3-(4-methylsulphonyl-phenyl)-propylamino)-, 2-(1-methyl-3-(3,4-dichloro-phenyl)-propylamino)-, 2-(1-methyl-3-(2,4-dichloro-phenyl)-propylamino)-, 2-(1-methyl-3-(2,5-dichloro-phenyl)-propylamino)-, 2-(1-methyl-3-(2,6-dichloro-phenyl)-propylamino)-, 2-(1-methyl-3-(2,6-difluoro-phenyl)-propylamino)-, 2-(1-methyl-3-(2,5-difluoro-phenyl)-propylamino)-, 2-(1-methyl-3-(2,4-difluoro-phenyl)-propylamino)-, 2-(1-methyl-3-(3,4-difluoro-phenyl)-propylamino)-, 2-(1-methyl-3-(3,5-difluoro-phenyl)-propylamino)-, 2-(1-methyl-3-(2-fluoro-4-chloro-phenyl)-propylamino)-, 2-(1-methyl-3-(4-fluoro-2-chloro-phenyl)-propylamino)-, 2-(1-methyl-3-(2,4-dimethyl-phenyl)-propylamino)-, 2-(1-methyl-3-(3,4-dimethyl-phenyl)-propylamino)-, 2-(1-methyl-3-(3,5-dimethyl-phenyl)-propylamino)-, 2-(1-methyl-3-(2,5-dimethyl-phenyl)-propylamino)-, 2-(1-methyl-3-(2-chloro-6-methyl-phenyl)-propylamino)-, 2-(1-methyl-3-(4-fluoro-2-methyl-phenyl)-propylamino)-, 2-(1-methyl-3-(2-fluoro-4-methyl-phenyl)-propylamino)-, 2-(1-methyl-3-(2-fluoro-5-methyl-phenyl)-propylamino)-, 2-(1-methyl-3-(5-fluoro-2-methyl-phenyl)-propylamino)-, 2-(1-methyl-3-thien-2-yl-propylamino)-, 2-(1-methyl-3-thien-3-yl-propylamino)-, 2-(1-methyl-3-pyridin-2-yl-propylamino)-, 2-(1-methyl-3-pyridin-3-yl-propylamino)- and 2-(1-methyl-3-pyridin-4-yl-propylamino)- -4-chloro-6-trifluoromethyl-1,3,5-triazine;

2-(1-methyl-3-phenyl-propylamino)-, 2-(1,2-dimethyl-3-phenyl-propylamino)-, 2-(1-methyl-3-(2-fluoro-phenyl)-propylamino)-, 2-(1-methyl-3-(3-fluoro-phenyl)-propylamino)-, 2-(1-methyl-3-(4-fluoro-phenyl)-propylamino)-, 2-(1-methyl-3-(2-chloro-phenyl)-propylamino)-, 2-(1-methyl-3-(3-chloro-phenyl)-propylamino)-, 2-(1-methyl-3-(4-chloro-phenyl)-propylamino)-, 2-(1-methyl-3-(2-bromo-phenyl)-propylamino)-, 2-(1-methyl-3-(3-bromo-phenyl)-propylamino)-, 2-(1-methyl-3-(4-bromo-phenyl)-propylamino)-, 2-(1-methyl-3-(2-nitro-phenyl)-propylamino)-, 2-(1-methyl-3-(3-nitro-phenyl)-propylamino)-, 2-(1-methyl-3-(4-nitro-phenyl)-propylamino)-, 2-(1-methyl-3-(2-methyl-phenyl)-propylamino)-, 2-(1-methyl-3-(3-methyl-phenyl)-propylamino)-, 2-(1-methyl-3-(4-methyl-phenyl)-propylamino)-, 2-(1-methyl-3-(2 -trifluoro-methyl-phenyl)-propylamino)-, 2-(1-methyl-3-(3-trifluoromethyl-phenyl)-propylamino)-, 2-(1-methyl-3-(4-trifluoromethyl-phenyl)-propylamino)-, 2-(1-methyl-3-(2-methoxy-phenyl)-propylamino)-, 2-(1-methyl-3-(3-methoxy-phenyl)-propylamiino)-, 2-(1-methyl-3-(4-methoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-trifluoromethoxy-phenyl)-propylamino)-, 1-(1-methyl-3-(3-trifluoromethoxy-phenyl)-propylamino)-, 2-(1-methyl-3-(4-trifluoromethoxy-phenyl)-propylamino)-, 2-(1-methyl-3-(2-methoxycarbonyl-phenyl)-propylamino)-, 2-(1-methyl-3-(2-ethoxycarbonyl-phenyl)-propylamino)-, 2-(1-methyl-3-(4-methoxycarbonyl-phenyl)-propylamino)-, 2-(1-methyl-3-(4-ethoxycarbonyl-phenyl)-propylamino)-, 2-(1-methyl-3-(2-methylthio-phenyl)-propylamino)-, 2-(1-methyl-3-(4-methylthio-phenyl)-propylamino)-, 2-(1-methyl-3-(2-methylsulphinyl-phenyl)-propylamino)-, 2-(1-methyl-3-(4-methylsulphinyl-phenyl)-propylamino)-, 2-(1-methyl-3-(2-methylsulphonyl-phenyl)-propylamino)-, 2-(1-methyl-3-(4-methylsulphonyl-phenyl)-propylamino)-, 2-(1-methyl-3-(3,4-dichloro-phenyl)-propylamino)-, 2-(1-methyl-3-(2,4-dichloro-phenyl)-propylamino)-, 2-(1-methyl-3-(2,5-dichloro-phenyl)-propylamino)-, 2-(1-methyl-3-(2,6-dichloro-phenyl)-propylamino)-, 2-(1-methyl-3-(2,6-difluoro-phenyl)-propylamino)-, 2-(1-methyl-3-(2,5-difluoro-phenyl)-propylamino)-, 2-(1-methyl-3-(2,4-difluoro-phenyl)-propylamino)-, 2-(1-methyl-3-(3,4-difluoro-phenyl)-propylamino)-, 2-(1-methyl-3-(3,5-difluoro-phenyl)-propylamino)-, 2-(1-methyl-3-(2-fluoro-4-chloro-phenyl)-propylamino)-, 2-(1-methyl-3-(4-fluoro-2-chloro-phenyl)-propylamino)-, 2-(1-methyl-3-(2,4-dimethyl-phenyl)-propylamino)-, 2-(1-methyl-3-(3,4-dimethyl-phenyl)-propylamino)-, 2-(1-methyl-3-(3,5-dimethyl-phenyl)-propylamino)-, 2-(1-methyl-3-(2,5-dimethyl-phenyl)-propylamino)-, 2-(1-methyl-3-(2-chloro-6-methyl-phenyl)-propylamino)-, 2-(1-methyl-3-(4-fluoro-2-methyl-phenyl)-propylamino)-, 2-(1-methyl-3-(2-fluoro-4-methyl-phenyl)-propylamino)-, 2-(1-methyl-3-(2-fluoro-5-methyl-phenyl)-propylamino)-, 2-(1-methyl-3-(5-fluoro-2-methyl-phenyl)-propylamino)-, 2-(1-methyl-3-thien-2-yl-propylamino)-, 2-(1-methyl-3-thien-3-yl-propylamino)-, 2-(1-methyl-3-pyridin-2-yl-propylamino)-, 2-(1-methyl-3-pyridin-3-yl-propyl-amino)- and 2-(1-methyl-3-pyridin-4-yl-propylamino)- -4-chloro-6-(1-fluoro-ethyl)-1,3,5-triazine; 2-(1-methyl-3-phenyl-propylamino)-, 2-(1,2- dimethyl-3-phenyl-propylamino)-, 2-(1-methyl-3-(2-fluoro-phenyl)-propylamino)-, 2-(1-methyl-3-(3-fluoro-phenyl)-propylamino)-, 2-(1-methyl-3-(4-fluoro-phenyl)-propylamino)-, 2-(1-methyl-3-(2-chloro-phenyl)-propylamino)-, 2-(1-methyl-3-(3-chloro-phenyl)-propylamino)-, 2-(1-methyl-3-(4-chloro-phenyl)-propylamino)-, 2-(1-methyl-3-(2-bromo-phenyl)-propylamino)-, 2-(1-methyl-3-(3-bromo-phenyl)-propylamino)-, 2-(1-methyl-3-(4-bromo-phenyl)-propylamino)-, 2-(1-methyl-3-(2-nitro-phenyl)-propylamino)-, 2-(1-methyl-3-(3-nitro-phenyl)-propylamino)-, 2-(1-methyl-3-(4-nitro-phenyl)-propylamino)-, 2-(1-methyl-3-(2-methyl-phenyl)-propylamino)-, 2-(1-methyl-3-(3-methyl-phenyl)-propylamino)-, 2-(1-methyl-3-(4-methyl-phenyl)-propylamino)-, 2-(1-methyl-3-(2-trifluoromethyl-phenyl)-propylamino)-, 2-(1-methyl-3-(3-trifluoromethyl-phenyl)-propylamino)-, 2-(1-methyl-3-(4-trifluoromethyl-phenyl)-propylamino)-, 2-(1-methyl-3-(2-methoxy-phenyl)-propylamino)-, 2-(1-methyl-3-(3-methoxy-phenyl)-propylaamino)-, 2-(1-methyl-3-(4-methoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-trifluoromethoxy-phenyl)-propylamino)-, 1-(1-methyl-3-(3-trifluoromethoxy-phenyl)-propylamino)-, 2-(1-methyl-3-(4-trifluoromethoxy-phenyl)-propylamino)-, 2-(1-methyl-3-(2-methoxycarbonyl-phenyl)-propylamino)-, 2-(1-methyl-3-(2-ethoxycarbonyl-phenyl)-propylamino)-, 2-(1-methyl-3-(4-methoxycarbonyl-phenyl)-propylamino)-, 2-(1-methyl-3-(4-ethoxycarbonyl-phenyl)-propylamino)-, 2-(1-methyl-3-(2-methylthio-phenyl)-propylamino)-, 2-(1-methyl-3-(4-methylthio-phenyl)-propylamino)-, 2-(1-methyl-3-(2-methylsulphinyl-phenyl)-propylamino)-, 2-(1-methyl-3-(4-methylsulphinyl-phenyl)-propylamino)-, 2-(1-methyl-3-(2-methylsulphonyl-phenyl)-propylamino)-, 2-(1-methyl-3-(4-methylsulphonyl-phenyl)-propylamino)-, 2-(1-methyl-3-(3,4-dichloro-phenyl)-propylamino)-, 2-(1-methyl-3-(2,4-dichloro-phenyl)-propylamino)-, 2-(1-methyl-3-(2,5-dichloro-phenyl)-propylamino)-, 2-(1-methyl-3-(2,6-dichloro-phenyl)-propylamino)-, 2-(1-methyl-3-(2,6-difluoro-phenyl)-propylamino)-, 2-(1-methyl-3-(2,5-difluoro-phenyl)-propylamino)-, 2-(1-methyl-3-(2,4-difluoro-phenyl)-propylamino)-, 2-(1-methyl-3-(3,4-difluoro-phenyl)-propylamino)-, 2-(1-methyl-3-(3,5-difluoro-phenyl)-propylamino)-, 2-(1-methyl-3-(2-fluoro-4-chloro-phenyl)-propylamino)-, 2-(1-methyl-3-(4-fluoro-2-chloro-phenyl)-propylamino)-, 2-(1-methyl-3-(2,4-dimethyl-phenyl)-propylamino)-, 2-(1-methyl-3-(3,4-dimethyl-phenyl)-propylamino)-, 2-(1-methyl-3-(3,5-dimethyl-phenyl)-propylamino)-, 2-(1-methyl-3-(2,5-dimethyl-phenyl)-propylamino)-, 2-(1-methyl-3-(2-chloro-6-methyl-phenyl)-propylamino)-, 2-(1-methyl-3-(4-fluoro-2-methyl-phenyl)-propylamino)-, 2-(1-methyl-3-(2-fluoro-4-methyl-phenyl)-propylamino)-, 2-(1-methyl-3-(2-fluoro-5-methyl-phenyl)-propylamino)-, 2-(1-methyl-3-(5-fluoro-2-methyl-phenyl)-propylamino)-, 2-(1-methyl-3-thien-2-yl-propylamino)-, 2-(1-methyl-3-thien-3-yl-propylamino)-, 2-(1-methyl-3-pyridin-2-yl-propylamino)-, 2-(1-methyl-3-pyridin-3-yl-propylamino)- and 2-(1-methyl-3-pyridin-4-yl-propylamino)- -4-chloro-6-(1-fluoro-1-methyl-ethyl)-1,3,5-triazine;

2-(1-methyl-3-phenyl-propylamino)-, 2-(1,2-dimethyl-3-phenyl-propylamino)-, 2-(1-methyl-3-(2-fluoro-phenyl)-propylamino)-, 2-(1-methyl-3-(3-fluoro-phenyl)-propylamino)-, 2-(1-methyl-3-(4-fluoro-phenyl)- propylamino)-, 2-(1-methyl-3-(2-chloro-phenyl)-propylamino)-, 2-(1-methyl-3-(3-chloro-phenyl)-propylamino)-, 2-(1-methyl-3-(4-chloro-phenyl)-propylamino)-, 2-(1-methyl-3-(2-bromo-phenyl)-propylamino)-, 2-(1-methyl-3-(3-bromo-phenyl)-propylamino)-, 2-(1-methyl-3-(4-bromo-phenyl)-propylamino)-, 2-(1-methyl-3-(2-nitro-phenyl)-propylamino)-, 2-(1-methyl-3-(3-nitro-phenyl)-propylamino)-, 2-(1-methyl-3-(4-nitro-phenyl)-propylamino)-, 2-(1-methyl-3-(2-methyl-phenyl)-propylaamino)-, 2-(1-methyl-3-(3-methyl-phenyl)-propylamino)-, 2-(1-methyl-3-(4-methyl-phenyl)-propylamino)-, 2-(1-methyl-3-(2-trifluoromethyl-phenyl)-propylamino)-, 2-(1-methyl-3-(3-trifluoromethyl-phenyl)-propylamino)-, 2-(1-methyl-3-(4-trifluoromethyl-phenyl)-propylamino)-, 2-(1-methyl-3-(2-methoxy-phenyl)-propylamino)-, 2-(1-methyl-3-(3-methoxy-phenyl)-propylamino)-, 2-(1-methyl-3-(4-methoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-trifluoromethoxy-phenyl)-propylamino)-, 1-(1-methyl-3-(3-trifluoromethoxy-phenyl)-propylamino)-, 2-(1-methyl-3-(4-trifluoromethoxy-phenyl)-propylamino)-, 2-(1-methyl-3-(2-methoxycarbonyl-phenyl)-propylamino)-, 2-(1-methyl-3-(2-ethoxycarbonyl-phenyl)-propylamino)-, 2-(1-methyl-3-(4-methoxycarbonyl-phenyl)-propylamino)-, 2-(1-methyl-3-(4-ethoxycarbonyl-phenyl)-propylamino)-, 2-(1-methyl-3-(2-methylthio-phenyl)-propylamino)-, 2-(1-methyl-3-(4-methylthio-phenyl)-propylamino)-, 2-(1-methyl-3-(2-methylsulphinyl-phenyl)-propylamino)-, 2-(1-methyl-3-(4-methylsulphinyl-phenyl)-propylamino)-, 2-(1-methyl-3-(2-methylsulphonyl-phenyl)-propylamino)-, 2-(1-methyl-3-(4-methylsulphonyl-phenyl)-propylamino)-, 2-(1-methyl-3-(3,4-dichloro-phenyl)-propylamino)-, 2-(1-methyl-3-(2,4-dichloro-phenyl)-propylamino)-, 2-(1-methyl-3-(2,5-dichloro-phenyl)-propylamino)-, 2-(1-methyl-3-(2,6-dichloro-phenyl)-propylamino)-, 2-(1-methyl-3-(2,6-difluoro-phenyl)-propylamino)-, 2-(1-methyl-3-(2,5-difluoro-phenyl)-propylamino)-, 2-(1-methyl-3-(2,4-difluoro-phenyl)-propylamino)-, 2-(1-methyl-3-(3,4-difluoro-phenyl)-propylamino)-, 2-(1-methyl-3-(3,5-difluoro-phenyl)-propylamino)-, 2-(1-methyl-3-(2-fluoro-4-chloro-phenyl)-propylamino)-, 2-(1-methyl-3-(4-fluoro-2-chloro-phenyl)-propylamino)-, 2-(1-methyl-3-(2,4-dimethyl-phenyl)-propylamino)-, 2-(1-methyl-3-(3,4-dimethyl-phenyl)-propylamino)-, 2-(1-methyl-3-(3,5-dimethyl-phenyl)-propylamino)-, 2-(1-methyl-3-(2,5-dimethyl-phenyl)-propylamino)-, 2-(1-methyl-3-(2-chloro-6-methyl-phenyl)-propylamino)-, 2-(1-methyl-3-(4-fluoro-2-methyl-phenyl)-propylamino)-, 2-(1-methyl-3-(2-fluoro-4-methyl-phenyl)-propylamino)-, 2-(1-methyl-3-(2-fluoro-5-methyl-phenyl)-propylamino)-, 2-(1-methyl-3-(5-fluoro-2-methyl-phenyl)-propylamino)-, 2-(1-methyl-3-thien-2-yl-propylamino)-, 2-(1-methyl-3-thien-3-yl-propylamino)-, 2-(1-methyl-3-pyridin-2-yl-propylamino)-, 2-(1-methyl-3-pyridin-3-yl-propylamino)- and 2-(1-methyl-3-pyridin-4-yl-propylamino)- -4-chloro-6-methoxy-1,3,5-triazine;

2-(1-Methyl-3-phenyl-propylamino)-, 2-(1,2-dimethyl-3-phenyl-propylamino)-, 2-(1-methyl-3-(2-fluoro-phenyl)-propylamino)-, 2-(1-methyl-3-(3-fluoro-phenyl)-propylamino)-, 2-(1-methyl-3-(4-fluoro-phenyl)-propylamino)-, 2-(1-methyl-3-(2-chloro-phenyl)-propylamino)-, 2-(1-methyl-3-(3-chloro-phenyl)-propylamino)-, 2-(1-methyl-3-(4-chloro-phenyl)-propylamino)-, 2-(1-methyl-3-(2-bromo-phenyl)-propylamino)-, 2-(1-methyl-3-(3-bromo-phenyl)-propylamino)-, 2-(1-methyl-3-(4-bromo-phenyl)-propylamino)-, 2-(1-methyl-3-(2-nitro-phenyl)-propylamino)-, 2-(1-methyl-3-(3-nitro-phenyl)-propylamino)-, 2-(1-methyl-3-(4-nitro-phenyl)-propylamino)-, 2-(1-methyl-3-(2-methyl-phenyl)-propylamino)-, 2-(1-methyl-3-(3-methyl-phenyl)-propylamino)-, 2-(1-methyl-3-(4-methyl-phenyl)-propylamino)-, 2-(1-methyl-3-(2-trifluoromethyl-phenyl)-propylamino)-, 2-(1-methyl-3-(3-trifluoromethyl-phenyl)-propylamino)-, 2-(1-methyl-3-(4-trifluoromethyl-phenyl)-propylamino)-, 2-(1-methyl-3-(2-methoxy-phenyl)-propylamino)-, 2-(1-methyl-3-(3-methoxy-phenyl)-propylamino)-, 2-(1-methyl-3-(4-methoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-trifluoromethoxy-phenyl)-propylamino)-, 1-(1-methyl-3-(3-trifluoromethoxy-phenyl)-propylamino)-, 2-(1-methyl-3-(4-trifluoromethoxy-phenyl)-propylamino)-, 2-(1-methyl-3-(2-methoxycarbonyl-phenyl)-propylamino)-, 2-(1-methyl-3-(2-ethoxycarbonyl-phenyl)-propylamino)-, 2-(1-methyl-3-(4-methoxycarbonyl-phenyl)-propylamino)-, 2-(1-methyl-3-(4-ethoxycarbonyl-phenyl)-propylamino)-, 2-(1-methyl-3-(2-methylthio-phenyl)-propylamino)-, 2-(1-methyl-3-(4-methylthio-phenyl)-propylamino)-, 2-(1-methyl-3-(2-methylsulphinyl-phenyl)-propylamino)-, 2-(1-methyl-3-(4-methylsulphinyl-phenyl)-propylamino)-, 2-(1-methyl-3-(2-methylsulphonyl-phenyl)-propylamino)-, 2-(1-methyl-3-(4-methylsulphonyl-phenyl)-propylamino)-, 2-(1-methyl-3-(3,4-dichloro-phenyl)-propylamino)-, 2-(1-methyl-3-(2,4-dichloro-phenyl)-propylamino)-, 2-(1-methyl-3-(2,5-dichloro-phenyl)-propylamino)-, 2-(1-methyl-3-(2,6-dichloro-phenyl)-propylamino)-, 2-(1-methyl-3-(2,6-difluoro-phenyl)-propylamino)-, 2-(1-methyl-3-(2,5-difluoro-phenyl)-propylamino)-, 2-(1-methyl-3-(2,4-difluoro-phenyl)-propylamino)-, 2-(1-methyl-3-(3,4-difluoro-phenyl)-propylamino)-, 2-(1-methyl-3-(3,5-difluoro-phenyl)-propylamino)-, 2-(1-methyl-3-(2-fluoro-4-chloro-phenyl)-propylamino)-, 2-(1-methyl-3-(4-fluoro-2-chloro-phenyl)-propylamino)-, 2-(1-methyl-3-(2,4-dimethyl-phenyl)-propylamino)-, 2-(1-methyl-3-(3,4-dimethyl-phenyl)-propylamino)-, 2-(1-methyl-3-(3,5-dimethyl-phenyl)-propylamino)-, 2-(1-methyl-3-(2,5-dimethyl-phenyl)-propylamino)-, 2-(1-methyl-3-(2-chloro-6-methyl-phenyl)-propylamino)-, 2-(1-methyl-3-(4-fluoro-2-methyl-phenyl)-propylamino)-, 2-(1-methyl-3-(2-fluoro-4-methyl-phenyl)-propylamino)-, 2-(1-methyl-3-(2-fluoro-5-methyl-phenyl)-propylamino)-, 2-(1-methyl-3-(5-fluoro-2-methyl-phenyl)-propylamino)-, 2-(1-methyl-3-thien-2-yl-propylamino)-, 2-(1-methyl-3-thien-3-yl-propylamino)-, 2-(1-methyl-3-pyridin-2-yl-propylamino)-, 2-(1-methyl-3-pyridin-3-yl-propylamino)- and 2-(1-methyl-3-pyridin-4-yl-propylamino)- -4-chloro-6-(2,2,2-trifluoroethoxy)-1,3,5-triazine;

2-(1-Methyl-3-phenyl-propylamino)-, 2-(1,2-dimethyl-3-phenyl-propylamino)-, 2-(1-methyl-3-(2-fluoro-phenyl)-propylamino)-, 2-(1-methyl-3-(3-fluoro-phenyl)-propylamino)-, 2-(1-methyl-3-(4-fluoro-phenyl)-propylamino)-, 2-(1-methyl-3-(2-chloro-phenyl)-propylamino)-, 2-(1-methyl-3-(3-chloro-phenyl)-propylamino)-, 2-(1-methyl-3-(4-chloro-phenyl)-propylamino)-, 2-(1-methyl-3-(2-bromo-phenyl)-propylamino)-, 2-(1-methyl-3-(3-bromo-phenyl)-propylamino)-, 2-(1-methyl-3-(4-bromo-phenyl)-propylamino)-, 2-(1-methyl-3-(2-nitro-phenyl)- propylamino)-, 2-(1-methyl-3-(3-nitro-phenyl)-propylamino)-, 2-(1-methyl-3-(4-nitro-phenyl)-propylamino)-, 2-(1-methyl-3-(2-methyl-phenyl)-propylamino)-, 2-(1-methyl-3-(3-methyl-phenyl)-propylamino)-, 2-(1-methyl-3-(4-methyl-phenyl)-propylamino)-, 2-(1-methyl-3-(2-trifluoromethyl-phenyl)-propylamino)-, 2-(1-methyl-3-(3-trifluoromethyl-phenyl)-propylamino)-, 2-(1-methyl-3-(4-trifluoromethyl-phenyl)-propylamino)-, 2-(1-methyl-3-(2-methoxy-phenyl)-propylamino)-, 2-(1-methyl-3-(3-methoxy-phenyl)-propylamino)-, 2-(1-methyl-3-(4-methoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-trifluoromethoxy-phenyl)-propylamino)-, 1-(1-methyl-3-(3-trifluoromethoxy-phenyl)-propylamino)-, 2-(1-methyl-3-(4-trifluoromethoxy-phenyl)-propylamino)-, 2-(1-methyl-3-(2-methoxycarbonyl-phenyl)-propylamino)-, 2-(1-methyl-3-(2-ethoxycarbonyl-phenyl)-propylamino)-, 2-(1-methyl-3-(4-methoxycarbonyl-phenyl)-propylamino)-, 2-(1-methyl-3-(4-ethoxycarbonyl-phenyl)-propylamino)-, 2-(1-methyl-3-(2-methylthio-phenyl)-propylamino)-, 2-(1-methyl-3-(4-methylthio-phenyl)-propylamino)-, 2-(1-methyl-3-(2-methylsulphinyl-phenyl)-propylamino)-, 2-(1-methyl-3-(4-methylsulphinyl-phenyl)-propylamino)-, 2-(1-methyl-3-(2-methylsulphonyl-phenyl)-propylamino)-, 2-(1-methyl-3-(4-methylsulphonyl-phenyl)-propylamino)-, 2-(1-methyl-3-(3, 4-dichloro-phenyl)-propylamino)-, 2-(1-methyl-3-(2,4-dichloro-phenyl)-propylamino)-, 2-(1-methyl-3-(2,5-dichloro-phenyl)-propylamino)-, 2-(1-methyl-3-(2,6-dichloro-phenyl)-propylamino)-, 2-(1-methyl-3-(2,6-difluoro-phenyl)-propylamino)-, 2-(1-methyl-3-(2,5-difluoro-phenyl)-propylamino)-, 2-(1-methyl-3-(2,4-difluoro-phenyl)-propylamino)-, 2-(1-methyl-3-(3,4-difluoro-phenyl)-propylamino)-, 2-(1-methyl-3-(3,5-difluoro-phenyl)-propylamino)-, 2-(1-methyl-3-(2-fluoro-4-chloro-phenyl)-propylamino)-, 2-(1-methyl-3-(4-fluoro-2-chloro-phenyl)-propylamino)-, 2-(1-methyl-3-(2,4-dimethyl-phenyl)-propylamino)-, 2-(1-methyl-3-(3,4-dimethyl-phenyl)-propylamiino)-, 2-(1-methyl-3-(3,5-dimethyl-phenyl)-propylamino)-, 2-(1-methyl-3-(2,5-dimethyl-phenyl)-propylamino)-, 2-(1-methyl-3-(2-chloro-6-methyl-phenyl)-propylamino)-, 2-(1-methyl-3-(4-fluoro-2-methyl-phenyl)-propylamino)-, 2-(1-methyl-3-(2-fluoro-4-methyl-phenyl)-propylamino)-, 2-(1-methyl-3-(2-fluoro-5-methyl-phenyl)-propylamino)-, 2-(1-methyl-3-(5-fluoro-2-methyl-phenyl)-propylamino)-, 2-(1-methyl-3-thien-2-yl-propylamino)-, 2-(1-methyl-3-thien-3-yl-propylamino)-, 2-(1-methyl-3-pyridin-2-yl-propylamino)-, 2-(1-methyl-3-pyridin-3-yl-propylamino)- and 2-(1-methyl-3-pyridin-4-yl-propylamino)- -4-chloro-6-methyl-thio-1,3,5-triazine;

2-(1-methyl-3-phenyl-propylamino)-, 2-(1,2-dimethyl-3-phenyl-propylamino)-, 2-(1-methyl-3-(2-fluoro-phenyl)-propylamino)-, 2-(1-methyl-3-(3-fluoro-phenyl)-propylamino)-, 2-(1-methyl-3-(4-fluoro-phenyl)-propylamino)-, 2-(1-methyl-3-(2-chloro-phenyl)-propylamino)-, 2-(1-methyl-3-(3-chloro-phenyl)-propylamino)-, 2-(1-methyl-3-(4-chloro-phenyl)-propylamino)-, 2-(1-methyl-3-(2-bromo-phenyl)-propylamino)-, 2-(1-methyl-3-(3-bromo-phenyl)-propylamino)-, 2-(1-methyl-3-(4-bromo-phenyl)-propylamino)-, 2-(1-methyl-3-(2-nitro-phenyl)-propylamino)-, 2-(1-methyl-3-(3-nitro-phenyl)-propylamino)-, 2-(1-methyl-3-(4-nitro-phenyl)-propylamino)-, 2-(1-methyl-3-(2-methyl-phenyl)-propylamino)-, 2-(1-methyl-3-(3-methyl-phenyl)-propylamino)-, 2-(1-methyl-3-(4-methyl-phenyl)-propylamino)-, 2-(1-methyl-3-(2-trifluoromethyl-phenyl)-propylamino)-, 2-(1-methyl-3-(3-trifluoromethyl-phenyl)-propylamino)-, 2-(1-methyl-3-(4-trifluoromethyl-phenyl)-propylamino)-, 2-(1-methyl-3-(2-methoxy-phenyl)-propylamino)-, 2-(1-methyl-3-(3-methoxy-phenyl)-propylamino)-, 2-(1-methyl-3-(4-methoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-trifluoromethoxy-phenyl)-propylamino)-, 1-(1-methyl-3-(3-trifluoromethoxy-phenyl)-propylamino)-, 2-(1-methyl-3-(4-trifluoromethoxy-phenyl)-propylamino)-, 2 -(1-methyl-3-(2-methoxycarbonyl-phenyl)-propylamino)-, 2-(1-methyl-3-(2-ethoxycarbonyl-phenyl)-propylamino)-, 2-(1-methyl-3-(4-methoxycarbonyl-phenyl)-propylamino)-, 2-(1-methyl-3-(4-ethoxycarbonyl-phenyl)-propylamino)-, 2-(1-methyl-3-(2-methylthio-phenyl)-propylamino)-, 2-(1-methyl-3-(4-methylthio-phenyl)-propylamino)-, 2-(1-methyl-3-(2-methylsulphinyl-phenyl)-propylamino)-, 2-(1-methyl-3-(4-methylsulphinyl-phenyl)-propylamino)-, 2-(1-methyl-3-(2-methylsulphonyl-phenyl)-propylamino)-, 2-(1-methyl-3-(4-methylsulphonyl-phenyl)-propylamino)-, 2-(1-methyl-3-(3, 4-dichloro-phenyl)-propylamino)-, 2-(1-methyl-3-(2,4-dichloro-phenyl)-propylamino)-, 2-(1-methyl-3-(2,5-dichloro-phenyl)-propylamino)-, 2-(1-methyl-3-(2,6-dichloro-phenyl)-propylamino)-, 2-(1-methyl-3-(2,6-difluoro-phenyl)-propylamino)-, 2-(1-methyl-3-(2,5-difluoro-phenyl)-propylamino)-, 2-(1-methyl-3-(2,4-difluoro-phenyl)-propylamino)-, 2-(1-methyl-3-(3,4-difluoro-phenyl)-propylamino)-, 2-(1-methyl-3-(3,5-difluoro-phenyl)-propylamino)-, 2-(1-methyl-3-(2-fluoro-4-chloro-phenyl)-propylamino)-, 2-(1-methyl-3-(4-fluoro-2-chloro-phenyl)-propylamino)-, 2-(1-methyl-3-(2,4-dimethyl-phenyl)-propylamino)-, 2-(1-methyl-3-(3,4-dimethyl-phenyl)-propylamino)-, 2-(1-methyl-3-(3,5-dimethyl-phenyl)-propylamino)-, 2-(1-methyl-3-(2,5-dimethyl-phenyl)-propylamino)-, 2-(1-methyl-3-(2-chloro-6-methyl-phenyl)-propylamino)-, 2-(1-methyl-3-(4-fluoro-2-methyl-phenyl)-propylamino)-, 2-(1-methyl-3-(2-fluoro-2-methyl-phenyl)-propylamino)-, 2-(1-methyl-3-(2-fluoro-4-methyl-phenyl)-propylamino)-, 2-(1-methyl-3-(2-fluoro-5-methyl-phenyl)-propylamino)-, 2-(1-methyl-3-(5-fluoro-2-methyl-phenyl)-propylamino)-, 2-(1-methyl-3-thien-2-yl-propylamino)-, 2-(1-methyl-3-thien-3-yl-propylamino)-, 2-(1-methyl-3-pyridin-2-yl-propylamino)-, 2-(1-methyl-3-pyridin-3-yl-propylamino)- and 2-(1-methyl-3-pyridin-4-yl-propylamino)- -4-chloro-6-methylsulphinyl-1,3,5-triazine;

2-(1-Methyl-3-phenyl-propylamino)-, 2-(1,2-dimethyl-3-phenyl-propylamino)-, 2-(1-methyl-3-(2-fluoro-phenyl)-propylamino)-, 2-(1-methyl-3-(3-fluoro-phenyl)-propylamino)-, 2-(1-methyl-3-(4-fluoro-phenyl)-propylamino)-, 2-(1-methyl-3-(2-chloro-phenyl)-propylamino)-, 2-(1-methyl-3-(3-chloro-phenyl)-propylamino)-, 2-(1-methyl-3-(4-chloro-phenyl)-propylamino)-, 2-(1-methyl-3-(2-bromo-phenyl)-propylamino)-, 2-(1-methyl-3-(3-bromo-phenyl)-propylamino)-, 2-(1-methyl-3-(4-bromo-phenyl)-propylamino)-, 2-(1-methyl-3-(2-nitro-phenyl)-propylamino)-, 2-(1-methyl-3-(3 -nitro-phenyl)-propylamino)-, 2-(1-methyl-3-(4-nitro-phenyl)-propylamino)-, 2-(1-methyl-3-(2-methyl-phenyl)-propylaamino)-, 2-(1-methyl-3-(3-methyl-phenyl)-propylamino)-, 2-(1-methyl-3-(4-methyl-phenyl)-propylamino)-, 2-(1-methyl-3-(2-trifluoromethyl-phenyl)-propylamino)-, 2-(1-methyl-3-(3-trifluoromethyl-phenyl)-propylamino)-, 2-(1-methyl-3-(4-trifluoromethyl-phenyl)- propylamino)-, 2-(1-methyl-3-(2-methoxy-phenyl)-propylamino)-, 2-(1-methyl-3-(3-methoxy-phenyl)-propylamino)-, 2-(1-methyl-3-(4-methoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-difluoromethoxy-phenyl)-propylamino)-, 2-(1-methyl-3-(2-trifluoromethoxy-phenyl)-propylamino)-, 1-(1-methyl-3-(3-trifluoromethoxy-phenyl)-propylamino)-, 2-(1-methyl-3-(4-trifluoromethoxy-phenyl)-propylamino)-, 2-(1-methyl-3-(2-methoxycarbonyl-phenyl)-propylamino)-, 2-(1-methyl-3-(2-ethoxycarbonyl-phenyl)-propylamino)-, 2-(1-methyl-3-(4-methoxycarbonyl-phenyl)-propylamino)-, 2-(1-methyl-3-(4-ethoxycarbonyl-phenyl)-propylamino)-, 2-(1-methyl-3-(2-methylthio-phenyl)-propylamino)-, 2-(1-methyl-3-(4-methylthio-phenyl)-propylamino)-, 2-(1-methyl-3-(2-methylsulphinyl-phenyl)-propylamino)-, 2-(1-methyl-3-(4-methylsulphinyl-phenyl)-propylamino)-, 2-(1-methyl-3-(2-methylsulphonyl-phenyl)propylamino)-, 2-(1-methyl-3-(4-methylsulphonyl-phenyl)-propylamino)-, 2-(1-methyl-3-(3,4-dichloro-phenyl)-propylamino)-, 2-(1-methyl-3-(2,4-dichloro-phenyl)-propylamino)-, 2-(1-methyl-3-(2,5-dichloro-phenyl)-propylamino)-, 2-(1-methyl-3-(2,6-dichloro-phenyl)-propylamino)-, 2-(1-methyl-3-(2,6-difluoro-phenyl)-propylamino)-, 2-(1-methyl-3-(2,5-difluoro-phenyl)-propylamino)-, 2-(1-methyl-3-(2,4-difluoro-phenyl)-propylamino)-, 2-(1-methyl-3-(3,4-difluoro-phenyl)-propylamino)-, 2-(1-methyl-3-(3,5-difluoro-phenyl)-propylamino)-, 2-(1-methyl-3-(2-fluoro-4-chloro-phenyl)-propylamino)-, 2-(1-methyl-3-(4-fluoro-2-chloro-phenyl)-propylamino)-, 2-(1-methyl-3-(2,4-dimethyl-phenyl)-propylamino)-, 2-(1-methyl-3-(3,4-dimethyl-phenyl)-propylamino)-, 2-(1-methyl-3-(3,5-dimethyl-phenyl)-propylamino)-, 2-(1-methyl-3-(2,5-dimethyl-phenyl)-propylamino)-, 2-(1-methyl-3-(2-chloro-6-methyl-phenyl)-propylamino)-, 2-(1-methyl-3-(4-fluoro-2-methyl-phenyl)-propylamino)-, 2-(1-methyl-3-(2-fluoro-4-methyl-phenyl)-propylamino)-, 2-(1-methyl-3-(2-fluoro-5-methyl-phenyl)-propylamino)-, 2-(1-methyl-3-(5-fluoro-2-methyl-phenyl)-propylamino)-, 2-(1-methyl-3-thien-2-yl-propylamino)-, 2-(1-methyl-3-thien-3-yl-propylamino)-, 2-(1-methyl-3-pyridin-2-yl-propylamino)-, 2-(1-methyl-3-pyridin-3-yl-propylamino)- and 2-(1-methyl-3-pyridin-4-yl-propylamino)- -4-chloro-6-methylsulphonyl-1,3,5-triazine.

The starting materials of the general formula (IV) have hitherto not been disclosed in the literature; as novel substances, they also form part of the subject-matter of the present application.

The novel substituted triazines of the general formula (IV) are obtained when triazines of the general formula (VIII)

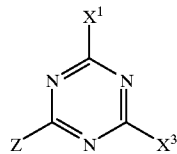

(VIII)

in which
$X^1$ and Z are each as defined above and
$X^3$ represents halogen
are reacted with substituted alkyl amino compounds of the general formula (VI)

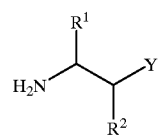

(VI)

in which
$R^1$, $R^2$ and Y are each as defined above, if appropriate in the presence of an acid acceptor, such as, for example, ethyldiisopropylamine, and if appropriate in the presence of a diluent, such as, for example, tetrahydrofuran or dioxane, at temperatures between −50° C. and +50° C. (cf. the Preparation Examples).

The formula (V) provides a general definition of the substituted aminotriazines to be used as starting materials in the process (c) according to the invention for preparing compounds of the formula (I). In the formula (V), Z preferably or in particular has that meaning which has already been mentioned above, in connection with the description of the compounds of the formula (I) according to the invention, as being preferred or as being particularly preferred for that; $X^2$ preferably represents fluorine, chlorine, bromine, methoxy or ethoxy, and in particular represents chlorine or methoxy.

The starting materials of the general formula (V) are known and/or can be prepared by processes known per se (cf. WO 95/11237).

The formula (VI) provides a general definition of the substituted alkylamines further to be used as starting materials in the process (c) according to the invention. In the formula (VI), $R^1$, $R^2$ and Y each preferably or in particular have those meanings which have already been mentioned above, in connection with the description of the compounds of the formula (IV) according to the invention, as being preferred or as being particularly preferred for $R^1$, $R^2$ and Y.

The starting materials of the general formula (VI) are known and/or can be prepared by processes known per se (cf. DE 3426919; DE 4000610; DE 4332738, EP 320898; EP 443606; Tetrahedron: Asymmetry 5 (1994), 817–820; Tetrahedron Lett. 29 (1988), 223–224; loc. cit. 36 (1995), 3917–3920; Preparation Examples).

If appropriate, the processes according to the invention for preparing the compounds of the formula (I) are carried out using a reaction auxiliary. Suitable reaction auxiliaries for the processes (a), (b) and (c) are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylmine, N,N-dimethyl-cyclohexylamine, dicyclohexylamine, ethyl-dicyclohexylamine, N,N-dimethylaniline, N,N-dimethyl-benzylamine, pyridine, 2-methyl-, 3-methyl-, 4-ethyl-, 2,4-dimethyl-, 2,6- dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo-[2,2,2]-octane (DABCO), 1,5-diazabicyclo[4,3,0]-non-5-ene (DBN), or 1,8-diazabicyclo[5,4,0]-undec-7-ene (DBU).

Suitable diluents for carrying out the processes (a), (b) and (c) according to the invention are especially inert organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methylpyrrolidone or hexamethylphosphoric triamide; esters, such as methyl acetate, ethyl acetate, n- or -i- propyl acetate, n-, i-, s- or t-butyl acetate; sulphoxides, such as dimethyl sulphoxide; alcohols, such as methanol, ethanol, n- or i-propanol, n- i-, s- or t-butanol, ethylene glycol monomethyl ether, ethylene glycol monoethyl ether, diethylene glycol monomethyl ether, diethylene glycol monoethyl ether, mixtures thereof with water or pure water.

In the practice of the processes (a), (b) and (c) according to the invention, the reaction temperatures can be varied over a relatively wide range. Generally, the reaction is carried out at temperatures between 0° C. and 300° C., preferably between 10° C. and 250° C.

The processes (a), (b) and (c) according to the invention are generally carried out at atmospheric pressure. However, it is also possible to carry out the processes according to the invention under elevated or reduced pressure—generally between 0.1 bar and 10 bar.

In the practice of the processes according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred for several hours at the temperature required. Work-up is carried out by conventional methods (cf. the Preparation Examples).

The active compounds according to the invention can be used as defoliants, desiccants, haulm killers and, especially, as weed-killers. By weeds in the broadest sense, there are to be understood all plants which grow in locations where they are undesirable. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera and Phalaris.

Monocotyledonous crops of th e genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture land, and for the selective control of weeds in annual cultures.

The compounds of the formula (I) according to the invention are suitable in particular for selectively controlling monocotyledonous and dicotyledonous weeds in monocotyledonous and dikotyledonous crops, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.be and 95 per cent by w eight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amiidochlor, amidosulfuron, asulam, atrazine, azimsulfuron, benazolin, benfuresate, bensulfuron(-methyl), bentazon, benzofenap, benzoylprop-(-ethyl), bialaphos, bifenox, bromobutide, bromofenoxim, bromoxynil, butachlor, butylate, cafenstrole, carbetamide, chlomethoxyfen, chloramben, chloridazon, chlorimuron-(-ethyl), chlomitrofen, chlorsulfuron, chlortoluron, cinmethylin, cinosulfuron, clethodim, clodinafop-(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop (-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfuron(-methyl), ethofumesate, ethoxyfen, etobenzanid, fenoxaprop-ethyl, flamprop(-isopropyl), flamprop(-isopropyl-L), flamprop-(-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate-(-ammonium), glyphosate(-isopropylammonium), halosafen, haloxyfop(-ethoxyethyl), hexazinone, imazamethabenz- (-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron-(-methyl), molinate, monolinuron, naproanilide, napropamide, neburon, nicosulfuron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium) quinchlorac, quinmerac, quizalofop-(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron-(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the Examples below.

PREPARATION EXAMPLES

Example 1

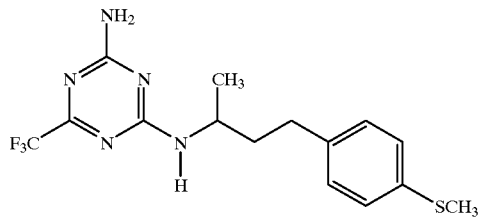

(Process (a))

At 20° C. to 30° C., a saturated solution of 6.0 g (0.11 mol) of sodium methoxide in methanol is added dropwise with stirring to a mixture of 31.5 g (0.10 mol) of (R/S)-1-(1-methyl-3-(4-methylthio-phenyl)-propyl)-biguanide hydrochloride (racemic), 15.5 g (0.10 mol) of ethyl trifluoroacetate and 150 ml of methanol and the reaction mixture is then stirred at approximately 20° C. for about 20 hours. The mixture is then diluted with methylene chloride to about three times its volume, washed with water and then with 1N aqueous sodium hydroxide solution, dried with sodium sulphate and filtered. The solvent is carefully distilled off from the filtrate using water pump vacuum.

This gives 12.1 g (34% of theory) of (R/S)-2-amino-4-(1-methyl-3-(4-methylthio-phenyl)-propylamino)-6-trifluoromethyl-1,3,5-triazine (racemate) as an amorphous residue.

Example 2

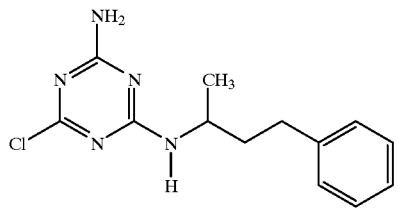

(Process (b))

At 20° C. to 30° C., 5.7 ml of a 25% strength aqueous solution of ammonia is added dropwise with stirring to a mixture of 5.4 g (18.2 mmol) of (R/S)-2,4-dichloro-6-(1-methyl-3-phenyl-propylamino)-1,3,5-triazine (racemic) and 35 ml of tetrahydrofuran and the reaction mixture is then stirred at approximately 20° C. for about 4 hours. The mixture is concentrated using water pump vacuum and the residue is then shaken with ethyl acetate/saturated aqueous sodium chloride solution, the organic phase is separated off and the aqueous phase is extracted with ethyl acetate; the organic phases are combined, dried with sodium sulphate and filtered. The filtrate is concentrated using water pump vacuum and the residue is crystallized by digestion with ethyl acetate/hexane. The crystalline product is then isolated by filtration with suction.

This gives 4.3 g (85% of theory) of (R/S)-2-amino-4-chloro-6-(1-methyl-3-phenyl-propylamino)-1,3,5-triazine (racemate) of melting point 115° C.

Example 3

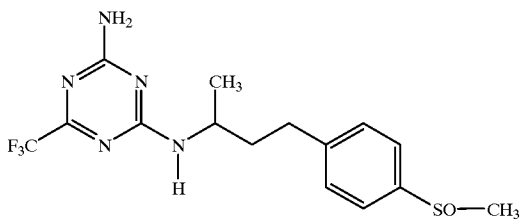

(Subsequent Reaction)

At 20° C. to 30° C., 4.6 g (about 17 mmol) of 3-chloro-perbenzoic acid (technical grade) are added with stirring to a mixture of 6.0 g (16.8 mmol) of (R/S)-2-amino-4-(1-methyl-3-(4-methylthio-phenyl)-propylamino)-6-trifluoromethyl-1,3,5-triazine (racemic) and 100 ml of dichloromethane and the reaction mixture is stirred at approximately 20° C. for 1 hour. The mixture is then filled up with water to give about twice its original volume and is made alkaline using ammonia water. The organic phase is then separated off, dried with sodium sulphate and filtered. The filtrate is concentrated using water pump vacuum and the residue is digested with ligroin/ethanol. The crystalline product is then isolated by filtration with suction.

This gives 4.2 g (67% of theory) of (R/S)-2-amino-4-(1-methyl-3-(4-methylsulphinyl-phenyl)-propylamino)-6-trifluoromethyl-1,3,5-triazine (racemate) of melting point 165° C.

Example 4

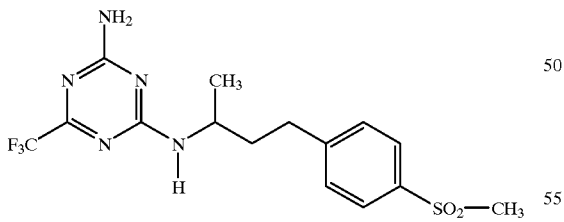

(Subsequent Reaction)

At 20° C. to 30° C., 14 g (about 55 mmol) of 3-chloro-perbenzoic acid (technical grade) are added with stirring to a mixture of 9.0 g (25 mmol) of (R¹ S) 2-amino-4-(1-methyl-3-(4-methylthio-phenyl)-propylamino)-6-trifluoromethyl-1,3,5-triazine (racemic) and 150 ml of dichloromethane and the reaction mixture is stirred at approximately 20° C. for 2 hours. The mixture is then filled up with water to about twice its original volume and made alkaline with ammonia water. The organic phase is then separated off, dried with sodium sulphate and filtered. The solvent is carefully distilled off from the filtrate using water pump vacuum.

This gives 9.0 g (92% of theory) of (R/S)-2-amino-4-(1-methyl-3-(4-methylsulphonyl-phenyl)-propylamino)-6-trifluoromethyl-1,3,5-triazine (racemate) as an amorphous residue.

Example 5

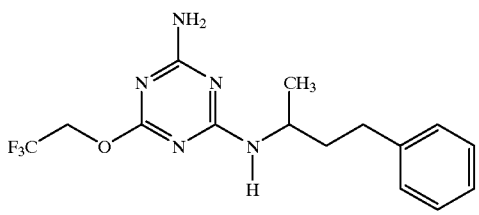

(Subsequent Reaction)

A mixture of 1.0 g (3.6 mmol) of (R/S)-2-amino-4-chloro-6-(1-methyl-3-phenyl-propylamino)-1,3,5-triazine (racemic), 0.84 g (7.5 mmol) of potassium t-butoxide, 10 ml of 2,2,2-trifluoro-ethanol and 5 ml of dioxane is stirred at approximately 70° C. for 4 hours and subsequently concentrated using water pump vacuum. The residue is shaken with ethyl acetate/water, the organic phase is separated off and the aqueous phase is re-extracted. The combined organic phases are dried with sodium sulphate and filtered. The solvent is carefully distilled off from the filtrate using water pump vacuum.

This gives 0.98 g (80% of theory) of (R/S)-2-amino-4-(2,2,2-trifluoro-ethoxy)-6-(1-methyl-3-phenyl-propylarnino)-1,3,5-triazine (racemate) as an amorphous residue.

By the methods of Preparation Examples 1 to 5 and in accordance with the general description of the preparation processes according to the invention, it is also possible to prepare, for example, the compounds of the formula (I) listed in Table 1 below.

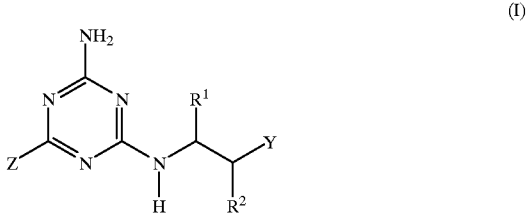

(I)

Table 1: examples of compounds of the formula (I) where $R^1$=CH$_3$ in the compounds listed in Table 1, $R^1$ always represents methyl and is therefore not mentioned for the individual examples in the table.

| Ex. No. | R² | Y | Z | Physical data and stereochemical specifications |
|---|---|---|---|---|
| 6 | H | 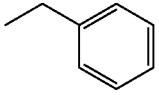 | OCH₃ | (amorphous) (racemate) |
| 7 | H | 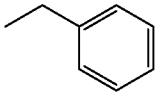 | SCH₃ | (amorphous) (racemate) |
| 8 | H | 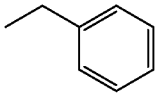 | CF(CH₃)₂ | (amorphous) (S enantiomer) $[\alpha]_D^{20} = -14.20°$ |
| 9 | H | 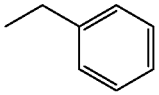 | CF(CH₃)₂ | (amorphous) (R enantiomer) $[\alpha]_D^{20} = +12.95°$ |
| 10 | CH₃ | 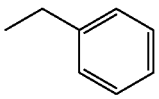 | CF(CH₃)₂ | (amorphous) (diastereomer mixture) |
| 11 | H | 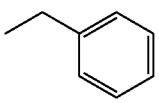 | CHFCH₃ | (amorphous) (R enantiomer) $[\alpha]_D^{20} = +27.59°$ |
| 12 | H | 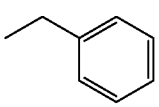 | CF₃ | (amorphous) (R enantiomer) $[\alpha]_D^{20} = +30.90°$ |
| 14 | H | 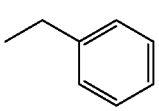 | CF₃ | (amorphous) (S enantiomer) $[\alpha]_D^{20} = -27.05°$ |
| 15 | H | 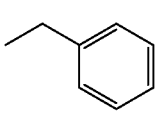 | CF(CH₃)₂ | (amorphous) (racemate) |
| 16 | H | 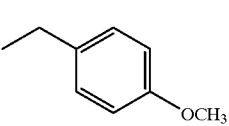 | CF₃ | M.p.: 68° C. (racemate) |
| 17 | H | 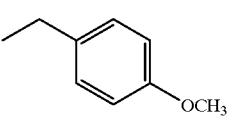 | CF₃ | (amorphous) (R enantiomer) |
| 18 | H | 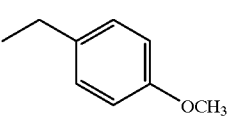 | CF₃ | (amorphous) (S enantiomer) |

-continued

| Ex. No. | R² | Y | Z | Physical data and stereochemical specifications |
|---|---|---|---|---|
| 19 | H | -CH₂-phenyl | C₂F₅ | (racemate) |
| 20 | H | -CH₂-phenyl | CHFCF₃ | (racemate) |
| 21 | H | -CH₂-phenyl | CHCl₂ | (racemate) |
| 22 | H | -CH₂-phenyl | CH₂Cl | (racemate) |
| 23 | H | -CH₂-phenyl | CCl₂CH₃ | (racemate) |
| 24 | H | -CH₂-phenyl | CHClCH₃ | (racemate) |
| 25 | H | -CH₂-phenyl | CH₂OCH₃ | (racemate) |
| 26 | H | -CH₂-(3,5-dimethylphenyl) | CF(CH₃)₂ | (racemate) |
| 27 | H | 5-methoxy-2-tert-butylpyrimidin-4-yl-oxy | CF₃ | (racemate) |
| 28 | H | 5-methoxy-2-tert-butylpyrimidin-4-yl-oxy | CH(CH₃)₂ | (racemate) |
| 29 | H | 5-methoxy-2-tert-butylpyrimidin-4-yl-oxy | CF(CH₃)₂ | (racemate) |

-continued

| Ex. No. | R² | Y | Z | Physical data and stereochemical specifications |
|---|---|---|---|---|
| 30 | H | 4-(SCH₃)-phenyl-ethyl | CHFCH₃ | (amorphous) (racemate) |
| 31 | H | 4-(SO-CH₃)-phenyl-ethyl | CHFCH₃ | (amorphous) (racemate) |
| 32 | H | 4-(SO₂-CH₃)-phenyl-ethyl | CHFCH₃ | (amorphous) (racemate) |
| 33 | H | 4-(SCH₃)-phenyl-ethyl | CF(CH₃)₂ | M.p.: 71° C. (racemate) |
| 34 | H | 4-(SO-CH₃)-phenyl-ethyl | CF(CH₃)₂ | (amorphous) (racemate) |
| 35 | H | 4-(SO₂-CH₃)-phenyl-ethyl | CF(CH₃)₂ | (amorphous) (racemate) |
| 36 | H | 5-ethyl-2-chloro-pyridinyl | CF₃ | M.p.: 80° C. (racemate) |
| 37 | H | 5-ethyl-2-chloro-pyridinyl | CHFCH₃ | (amorphous) (racemate) |
| 38 | H | 5-ethyl-2-chloro-pyridinyl | CF(CH₃)₂ | (amorphous) (racemate) |
| 39 | H | 3-ethyl-pyridinyl | CF₃ | (amorphous) (racemate) |
| 40 | H | 3-ethyl-pyridinyl | CHFCH₃ | (amorphous) (racemate) |
| 41 | H | 4-ethyl-pyridinyl | CF(CH₃)₂ | (amorphous) (racemate) |

-continued

| Ex. No. | R² | Y | Z | Physical data and stereochemical specifications |
|---|---|---|---|---|
| 42 | H | 4-F-C₆H₄-CH₂CH₂- | CF(CH₃)₂ | (amorphous) (racemate) |
| 43 | H | 3,4-(CH₃)₂-C₆H₃-CH₂CH₂- | CF(CH₃)₂ | (amorphous) (racemate) |
| 44 | H | C₆H₅-CH₂CH₂- | CF₂CHF₂ | (racemate) |
| 45 | H | 2-CH₃-C₆H₄-CH₂CH₂- | CF(CH₃)₂ | (amorphous) (racemate) |
| 46 | H | 3-CH₃-C₆H₄-CH₂CH₂- | CF(CH₃)₂ | (amorphous) (racemate) |
| 47 | H | 4-CH₃-C₆H₄-CH₂CH₂- | CF(CH₃)₂ | (amorphous) (racemate) |
| 48 | H | 4-Cl-C₆H₄-CH₂CH₂- | CF(CH₃)₂ | M.p.: 92° C. (racemate) |
| 49 | H | 2-Cl-C₆H₄-CH₂CH₂- | CF(CH₃)₂ | (amorphous) (racemate) |
| 50 | H | 3-Cl-C₆H₄-CH₂CH₂- | CF(CH₃)₂ | (amorphous) (racemate) |
| 51 | H | C₆H₅-CH₂CH₂- | —CO—CH₃ | (amorphous) (Racemat |
| 52 | H | 3-thienyl-CH₂CH₂- | CF₃ | (amorphous) (racemate) |

-continued

| Ex. No. | R² | Y | Z | Physical data and stereochemical specifications |
|---|---|---|---|---|
| 53 | H | 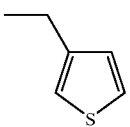 | CHFCH₃ | (amorphous) (racemate) |
| 54 | H | 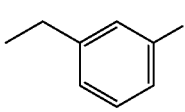 | CH₂OCH₃ | M.p.: 85° C. (racemate) |
| 55 | H | 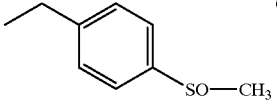 | CH₂OCH₃ | (amorphous) (racemate) |
| 56 | H | 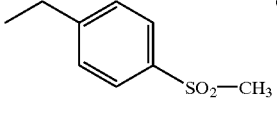 | CH₂OCH₃ | (amorphous) (racemate) |
| 57 | H | 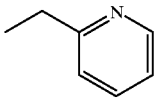 | CF₃ | (amorphous) (racemate) |
| 58 | H | 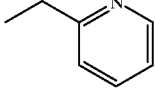 | CHFCH₃ | (amorphous) (racemate) |
| 59 | H | 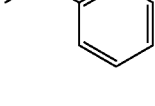 | CF(CH₃)₂ | (amorphous) (racemate) |
| 60 | H | 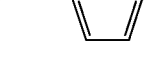 | CF₃ | (amorphous) (racemate) |
| 61 | H | 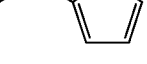 | CHFCH₃ | (amorphous) (racemate) |
| 62 | H | 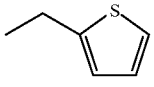 | CF(CH₃)₂ | (amorphous) (racemate) |
| 63 | H | 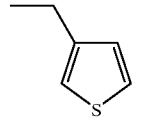 | CF(CH₃)₂ | (amorphous) (racemate) |
| 64 | H | 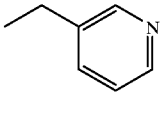 | CF(CH₃)₂ | (amorphous) (racemate) |

-continued

| Ex. No. | R² | Y | Z | Physical data and stereochemical specifications |
|---|---|---|---|---|
| 65 | H | 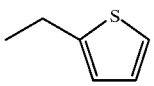 | CH₂OCH₃ | (amorphous) (racemate) |
| 66 | H | 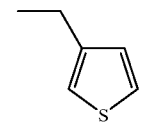 | CH₂OCH₃ | (amorphous) (racemate) |
| 67 | H | 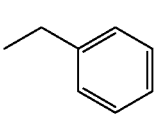 | CF₃ | (amorphous) (racemate) |
| 68 | H | 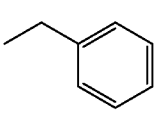 | CH(CH₃)₂ | $n_D^{20}$ = 1,5682 (racemate) |
| 69 | H | 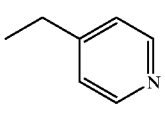 | CF₃ | (amorphous) (racemate) |
| 70 | H | 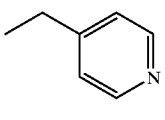 | CHFCH₃ | (amorphous) (racemate) |
| 71 | H | 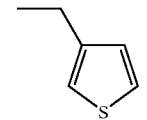 | CH₂CH₂OCH₃ | (amorphous) (racemate) |
| 72 | H | 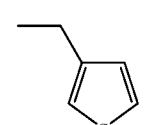 | CH₂CH(OCH₃)₂ | (amorphous) (racemate) |
| 73 | H | 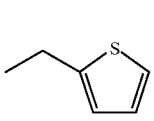 | CH₂CH₂OCH₃ | (amorphous) (racemate) |
| 74 | H | 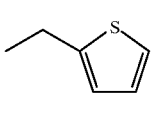 | CH₂CH(OCH₃)₂ | (amorphdus) (racemate) |
| 75 | H | 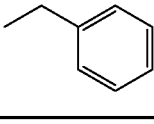 | CH(CH₃)(C₃H₇) | (amorphous) (racemate) |

Starting Materials of the Formula (II)

Example (II-I)

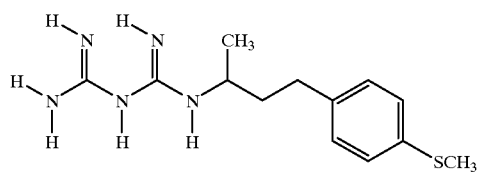 × HCl

At approximately 140° C. (internal temperature, bath temperature approximately 175° C.), a mixture of 23.2 g (0.10 mol) of (R/S)-1-methyl-3-(4-methylthio-phenyl)-propylamine hydrochloride (racemic), 8.5 g (0.10 mol) of dicyanodiamide (cyanoguanidine) and 100 ml of dichlorobenzene is stirred for 3 hours. The solvent is then carefully distilled off using oil pump vacuum.

The (R/S)-1-(1-methyl-3-(4-methylthio-phenyl)-propyl)-biguanide hydrochloride (racemate) is obtained as an amorphous residue which can be used for the reaction according to process (a) without further purification.

The reaction can be carried out at the same temperature even without solvent—i.e. in the melt.

By the method of Example (II-I), it is also possible to prepare, for example, the compounds of the formula (II) listed in Table 2 below, or their hydrochlorides.

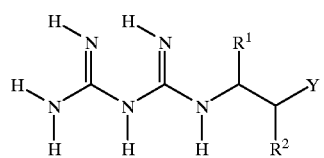 (II)

Table 2: examples of compounds of the formula (II), where $R^1=CH_3$ in all instances, these are the corresponding hydrochlorides!

| Ex. No. | $R^2$ | Y | Physical data and stereochemical specifications |
|---|---|---|---|
| II-2 | H | benzyl | (amorphous) (R enantiomer) |
| II-3 | H | benzyl | (amorphous) (S enantiomer) |
| II-4 | $CH_3$ | benzyl | (amorphous) (diastereomer mixture) |

Starting materials of the formula (IV)

Example (IV-1)

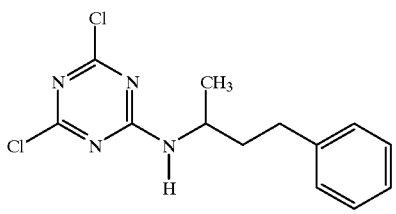

With stirring, a solution of 16.34 g (0.11 mol) of (R/S)-1-methyl-3-phenyl-propylamine and 14.2 g (0. 11 mol) of ethyldiisopropylamine in 20 ml of tetrahydrofuran is added to a mixture, cooled to −40° C. to −50° C., of 20.2 g (0.11 mol) of cyanuric chloride (2,4,6-trichloro-1,3,5-triazine) and 80 ml of tetrahydrofuran. The reaction mixture is stirred at the temperature mentioned above for 30 minutes and then for another 30 minutes at room temperature (approximately 20° C.). The mixture is concentrated and the residue is then shaken with diethyl ether/saturated aqueous ammonium chloride solution, the organic phase is separated off and the aqueous phase is re-extracted, the combined organic phases are dried with sodium sulphate and filtered. The filtrate is concentrated using water pump vacuum, the residue is digested with petroleum ether/methyl t-butyl ether and the crystalline product is isolated by filtration with suction.

This gives 27.5 g (84% of theory) (R/S)-2,4-dichloro-6-(1-methyl-3-phenyl-propylamino)-1,3,5-triazine (racemate) of melting point 79° C.

Starting Materials of the Formula (V)

Example (V-1)

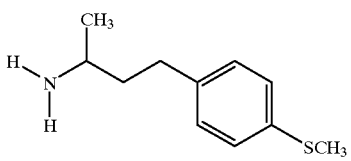

Step 1

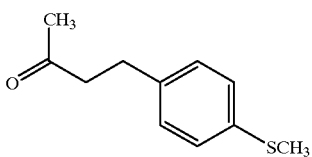

A mixture of 8.0 g (0.08 mol) of pentane-2,4-dione, 14.5 g (0.08 mol) of 4-methylthio-benzyl chloride, 12 g of potassium carbonate and 100 ml of ethanol is heated under reflux for 15 hours. After cooling, the mixture is diluted to about three times the original volume using approximately identical amounts by volume of water and methylene chloride, the organic phase is separated off after vigorous shaking, dried with sodium sulphate and filtered. The filtrate is concentrated using water pump vacuum and the residue is distilled using oil pump vacuum.

This gives 8.2 g (60% of theory) of 1-(4-methylthio-phenyl)-butan-3-one of boiling point 105° C. (at 2 mbar).

Step 2

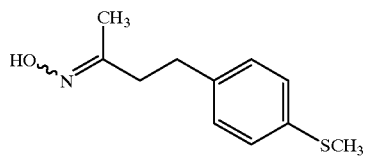

At room temperature (approximately 20° C.), 2.0 g of sodium hydroxide are added to a mixture of 7.2 g (0.04 mol) of 1-(4-methylthio-phenyl)-butan-3-one, 4.0 g hydroxylamine-hydrochloride (0.058 mol) and 50 ml of ethanol and the mixture is stirred at 20° C. to 35° C. for 2 hours. The mixture is diluted to about three times the original volume using approximately identical amounts by volume of water and methylene chloride and the organic phase is separated off after vigorous shaking, dried with sodium sulphate and filtered. The solvent is carefully distilled off from the filtrate using water pump vacuum.

This gives 4.0 g (48% of theory) of 1-(4-methylthio-phenyl)-butan-3-one oxime as a solid residue of melting point 71 ° C.

Step 3

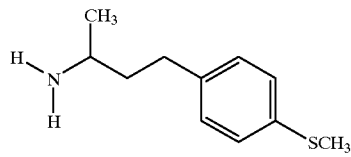

A solution of 63 g (0.3 mol) of 1-(4-methylthio-phenyl)-butan-3-one-oxime in 200 ml of tetrahydrofuran is added dropwise with stirring to a mixture of 25 g of lithium tetrahydridoaluminate (lithiumalanate, lithiumaluminium hydride) and 300 ml of tetrahydrofuran, the internal temperature rising from initially about 20° C. to approximately 60° C. The reaction mixture is then stirred under reflux for 5 hours. At 20° C. to 40° C., 100 ml of water are then added dropwise. The organic phase is then separated off, dried with sodium sulphate and filtered. The filtrate is concentrated using water pump vacuum and the residue is distilled using oil pump vacuum.

This gives 42 g (72% of theory) of (R/S)-1-methyl-3-(4-methylthio-phenyl)-propylamine (racemate) of melting point 112° C. (at 1 mbar).

Example (V-2)

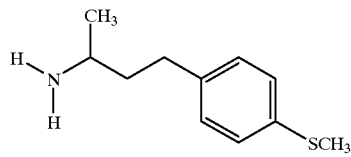

Step 1

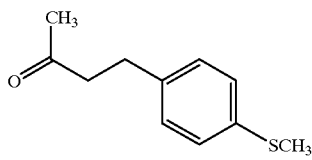

A mixture of 8.0 g (0.08 mol) of pentane-2,4-dione, 14.5 g (0.08 mol) of 4-methylthio-benzyl chloride, 12 g of potassium carbonate and 100 ml of ethanol is heated under reflux for 15 hours. After cooling, the mixture is diluted to about three times the original volume using approximately identical amounts by volume of water and methylene chloride, the organic phase is separated off after vigorous shaking, dried with sodium sulphate and filtered. The filtrate is concentrated using water pump vacuum and the residue is distilled using oil pump vacuum.

This gives 8.2 g (60% of theory) of 1-(4-methylthio-phenyl)-butan-3-one of boiling point 105° C. (at 2 mbar).

Step 2

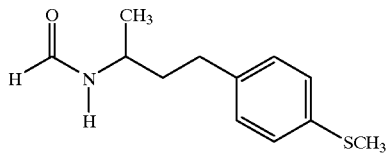

Over a period of approximately 60 minutes, 70 ml of formic acid are added dropwise with stirring to a mixture, heated to 140° C., of 83 g (0.46 mol) of 1-(4 -methylthio-phenyl)-butan-3-one, 300 ml formamide and 10 ml of formic acid. The reaction mixture is stirred at 140° C. to 150° C. for approximately 3 hours and, after cooling, diluted to about three times the original volume using identical amounts by volume of water and methylene chloride and shaken vigorously. The organic phase is then separated off, dried with sodium sulphate and filtered. The solvent is carefully distilled off from the filtrate using water pump vacuum.

This gives 94 g (92% of theory) of (R/S)-N-(1-methyl-3-(4-methylthio-phenyl)-propyl)-formamide (racemate) as an amorphous residue which can be used for the next step without further purification.

Step 3

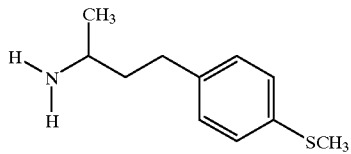

A mixture of 67 g (0.3 mol) of (R/S)-N-(1-methyl-3-(4-methylthio-phenyl)-propyl)-formamide (racemic) and 250 ml of conc. hydrochloric acid is heated under reflux for approximately 150 minutes. After cooling with ice-water, the mixture is made alkaline using 2N aqueous sodium hydroxide solution, shaken with methylene chloride, and the organic phase is separated off, dried with sodium sulphate and filtered. The filtrate is concentrated using water pump vacuum and the residue is distilled using oil pump vacuum.

This gives 40 g (68% of theory) of (R/S)-1-methyl-3-(4-methylthio-phenyl)-propylamine(racemate) of boiling point 105° C. (at 0.8 mbar).

Example (V-3)

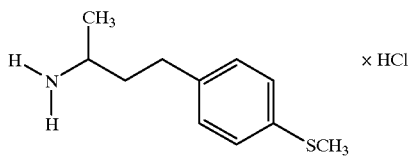

11 ml of 33% strength hydrochloric acid are added dropwise with stirring to a mixture of 20 g (0.1 mol) of (R|S)-1-methyl-3-(4-methylthio-phenyl)-propylamine (racemic) and 20 ml of water and the mixture is stirred at room temperature for approximately 1 further hour. The solvent is then carefully distilled off under water pump vacuum, giving (R/S)-1-methyl-3-(4-methylthio-phenyl)-propylamine hydrochloride (racemate) quantitatively as a solid residue.

Example (V-4)

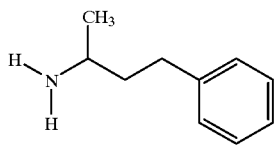

Isolation of the Enantiomers 11.9 g (0.08 Mol) of (R/S)-1-methyl-3-phenyl-propylamine are initially charged with 34 ml of methyl t-butyl ether and 8.32 g (0.08 mol) of methyl methoxy acetate and admixed with 0.42 g of Novozym-435®. The mixture is stirred at room temperature (approximately 20° C.) for 2 hours and then filtered and washed with 25 ml of methyl t-butyl ether. The filtrate is shaken three times with 30 ml of 10% strength aqueous hydrochloric acid each time and then dried with sodium sulphate and filtered. The solvent is carefully distilled off from the filtrate using water pump vacuum.

This gives 7.4 g (96.25 % ee, 84% of theory) of (R)-N-methoxyacetyl-1-methyl-3-phenyl-propylamine, which is then heated under reflux with 50 ml of 18% strength aqueous hydrochloric acid for 4 hours. Work-up gives 5.0 g (96% ee, 98% of theory) of (R)-1-methyl-3-phenyl-propylamine.

The three aqueous hydrochloric solutions obtained according to the above description are combined and made alkaline with ice-cooling using 10% strength aqueous sodium hydroxide solution. The mixture is then extracted three times with 50 ml of methylene chloride each time. The combined organic extract solutions are dried with sodium sulphate and filtered. The solvent is carefully distilled off from the filtrate using water pump vacuum.

This gives 4.1 g (71.3% ee, 69% of theory) of (S)-1-methyl-3-phenyl-propylamine as a solid residue.

Use Examples

Example A

Pre-emergence-test

| | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is watered with the preparation of active compound. The amount of water per unit area is advantageously kept constant. The concentration of active compound in the preparation is immaterial, only the application rate of active compound per unit area matters.

After three weeks, the degree of damage to the plants is scored visually in % damage in comparison to the development of the untreated control.

The Figures Denote:

| | |
|---|---|
| 0% = | no effect (like untreated control) |
| 100% = | total destruction |

In this test, the compounds of Preparation Examples 5, 7, 9, 11, 12, 15, 52, 53, 59, 60, 61, 62 and 63, for example, show strong activity against weeds, and some of them are tolerated well by crop plants, such as, for example, maize, wheat barley, rapeseed and cotton (cf. Table A).

In the tables below, „ai" means „active ingredient".

TABLE A

| | Pre-emergence-test/greenhouse | | | |
|---|---|---|---|---|
| Active compound of Preparation Ex. No. | Application rate (g of ai./ha) | Maize | Amaranthus | Galium |
| (7) | 1000 | 10 | 100 | 100 |

TABLE A-continued

Pre-emergence-test/greenhouse

| Active compound of Preparation Ex. No. | Application rate (g of ai./ha) | Abutilon | Amaranthus | Galium | Sinapis | Xanthium |
|---|---|---|---|---|---|---|
| (5) [structure: triazine with HN-CH(CH3)-CH2CH2-phenyl, O-CH2CF3, NH2] | 1000 | 80 | 100 | 80 | 80 | 90 |

| Active compound of Preparation Ex. No. | Application rate (g of ai./ha) | Barley | Cotton | Alopecurus | Digitaria | Echinochloa | Amaranthus | Datura | Matricaria | Viola |
|---|---|---|---|---|---|---|---|---|---|---|
| (9) [structure: triazine with C(CH3)2F, NH-CH(CH3)-CH2CH2-phenyl, NH2] | 125 | 0 | 0 | 95 | 90 | 95 | 100 | — | 100 | 100 |
| (11) [structure: triazine with phenyl-CH2CH2-CH(CH3)-NH, CHFCH3, NH2] | 250 | 15 | 0 | 100 | 100 | 95 | 100 | 100 | 100 | 100 |

| Active compound of Preparation Ex. No. | Application rate (g of ai./ha) | Barley | Rapeseed | Digitaria | Echinochloa | Amaranthus | Chenopodium | Matricaria | Viola |
|---|---|---|---|---|---|---|---|---|---|
| (12) [structure: triazine with CF3, HN-CH(CH3)-CH2CH2-phenyl, NH2] | 500 | 0 | 0 | 100 | 90 | 100 | 100 | — | 100 |

TABLE A-continued

Pre-emergence-test/greenhouse

| Structure | Application rate (g of ai./ha) | Wheat | Digitaria | Echinochloa | Amaranthus | Datura | Solanum | | |
|---|---|---|---|---|---|---|---|---|---|
| (15) | 125 | 0 | 0 | 100 | 90 | 100 | 100 | 100 | 100 |

| Active compound of Preparation Ex. No. | Application rate (g of ai./ha) | Wheat | Digitaria | Echinochloa | Amaranthus | Datura | Solanum |
|---|---|---|---|---|---|---|---|
| (52) | 500 | 0 | 100 | 100 | 100 | 100 | 100 |
| (53) | 250 | 0 | 100 | 100 | 100 | 100 | 100 |
| (60) | 500 | 0 | 100 | 100 | 100 | 95 | 100 |

TABLE A-continued

Pre-emergence-test/greenhouse

| Active compound of Preparation Ex. No. | Application rate (g of ai./ha) | Alopercus | Abutilon | Amaranthus |
|---|---|---|---|---|
| (59) | 1000 | 95 | 100 | 90 |

| Active compound of Preparation Ex. No. | Application rate (g of ai./ha) | Wheat | Cotton | Digitaria | Echinochloa | Amaranthus | Datura | Solanum |
|---|---|---|---|---|---|---|---|---|
| (61) | 250 | 0 | 0 | 90 | 100 | 80 | 100 | 100 |

| Active compound of Preparation Ex. No. | Application rate (g of ai./ha) | Barley | Digitaria | Echinochloa | Amaranthus | Datura | Solanum |
|---|---|---|---|---|---|---|---|
| (62) | 500 | 10 | 100 | 100 | 100 | 100 | 100 |

| Active compound of Preparation Ex. No. | Application rate (g of ai./ha) | Alopecurus | Setaria | Abutilon | Amaranthus | Galium |
|---|---|---|---|---|---|---|
| (63) | 1000 | 90 | 100 | 90 | 100 | 100 |

Example B

Post-emergence-test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound such that the particular amounts of active compounds desired are applied per unit area. The concentration of the spray liquor is chosen so that the particular amounts of active compound desired are applied in 1000 l of water/ha.

After three weeks, the degree of damage to the plants is scored visually in % damage in comparison to the untreated control.

The Figures Denote:

| 0% = | no effect (like untreated control) |
|---|---|
| 100% = | total destruction |

In this test, the compounds of Preparation Examples 2, 6, 7, 8, 9, 10, 11, 12, 13, 14, 15, 16, 18, 52, 53, 60, 61, 62, 63 and 67, for example, show strong activity against weeds, and some of them are tolerated well by crop plants, such as, for example, maize, wheat, barley and rapeseed (cf. Table B).

TABLE B

Post-emergence-test/greenhouse

| Active compound of Preparation Ex. No | Application rate (g ai./ha) | Amaranthus | Sinapis |
|---|---|---|---|
| (2) [structure: 6-chloro-N-(1-methyl-3-phenylpropyl)-1,3,5-triazine-2,4-diamine] | 1000 | 100 | 100 |
| (6) [structure: 6-methoxy-N-(1-methyl-3-phenylpropyl)-1,3,5-triazine-2,4-diamine] | 1000 | 100 | 95 |

| Active compound of Preparation Ex. No | Application rate (g ai./ha) | Wheat | Rape-seed | Ama-ranthus | Cheno-podium | Ipo-moea | Poly-gonum | Solanum |
|---|---|---|---|---|---|---|---|---|
| (7) [structure: 6-methylthio-N-(1-methyl-3-phenylpropyl)-1,3,5-triazine-2,4-diamine] | 125 | 0 | 0 | 100 | 100 | 100 | 100 | 100 |

TABLE B-continued

Post-emergence-test/greenhouse

| Active compound of Preparation Ex. No | Application rate (g ai./ha) | Wheat | Echino-chloa | Set-aria | Ama-ran-thus | Cheno-podium | Ipo-moea | Poly-gonum | Sola-num |
|---|---|---|---|---|---|---|---|---|---|
| 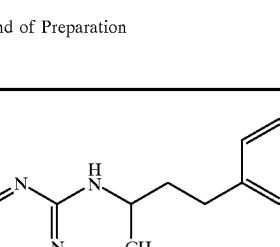<br>(8) [S-Enantiomer] | 250 | 10 | 80 | 90 | 95 | 95 | 95 | 95 | 95 |

| Active compound of Preparation Ex. No | Application rate (g ai/ha) | Cyperus | Amaranthus | Galium | Sinapis |
|---|---|---|---|---|---|
| 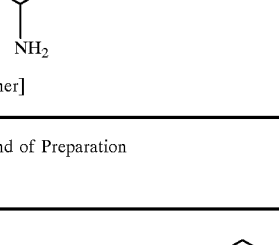<br>(9) [R-Enantiomer] | 1000 | 90 | 100 | 80 | 100 |

| Active compound of Preparation Ex. No | Application rate (g ai./ha) | Maize | Ama-ranthus | Datura | Ipomoea | Poly-gonum | Veronica |
|---|---|---|---|---|---|---|---|
| 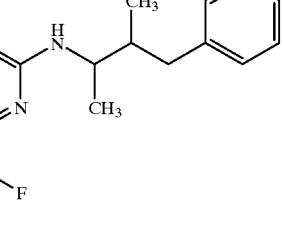<br>(10) | 250 | 10 | 95 | 100 | 100 | 100 | 100 |

| Active compound of Preparation Ex. No | Application rate (g ai./ha) | Wheat | Ama-ranthus | Cheno-podium | Datura | Ipo-moea | Poly-gonum | Solanum |
|---|---|---|---|---|---|---|---|---|
| 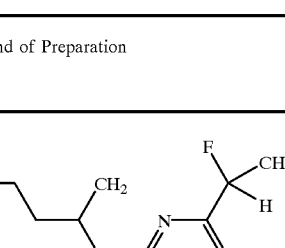<br>(11) | 125 | 30 | 95 | 100 | 100 | 95 | 100 | 100 |

TABLE B-continued
Post-emergence-test/greenhouse
| | | | | | | | | |
|---|---|---|---|---|---|---|---|---|
| 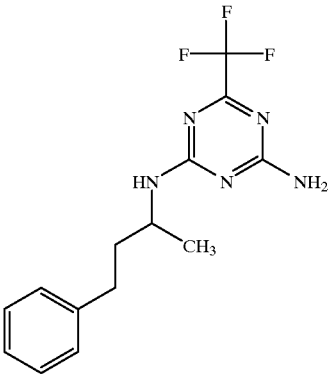 (12) | | 250 | 0 | 100 | 100 | 100 | 95 | 100 | 100 |
| 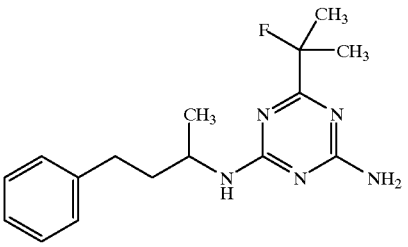 (15) | | 250 | 0 | 95 | 95 | 100 | 100 | 100 | 100 |
| Active compound of Preparation Ex. No | Application rate (g ai./ha) | Setaria | Abutilon | Amaranthus | Galium | Sinapis | Xanthium |
|---|---|---|---|---|---|---|---|
| 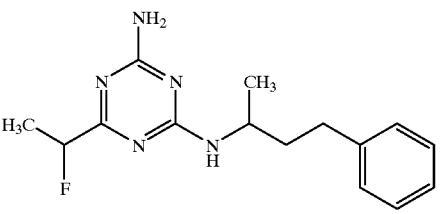 (13) | 1000 | 100 | 100 | 100 | 100 | 100 | 100 |
| 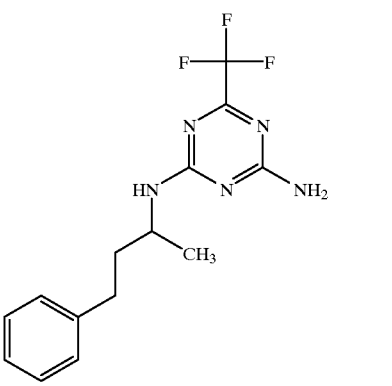 (14) | 1000 | 100 | 100 | 100 | 100 | 100 | 100 |

TABLE B-continued

Post-emergence-test/greenhouse

| Active compound of Preparation Ex. No | Application rate (g ai./ha) | Barley | Echinochloa | Setaria | Amaranthus | Chenopodium | Viola |
|---|---|---|---|---|---|---|---|
| 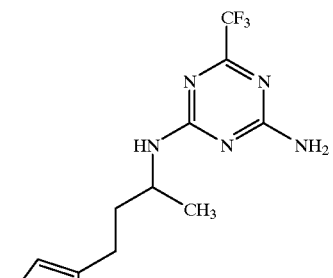 (52) | 500 | 10 | 100 | 95 | 100 | 100 | 100 |

| Active compound of Preparation Ex. No | Application rate (g ai./ha) | Echinochloa | Setaria | Amaranthus | Chenopodium | Viola |
|---|---|---|---|---|---|---|
| 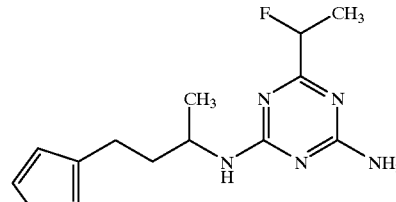 (53) | 500 | 100 | 90 | 100 | 100 | 100 |
| 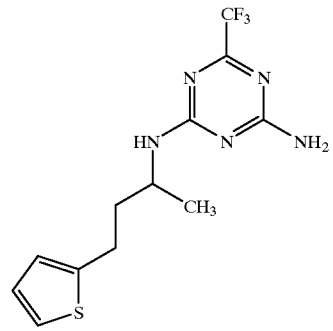 (60) | 500 | 100 | 100 | 100 | 100 | 100 |

| Active compound of Preparation Ex. No | Application rate (g ai./ha) | Digitaria | Setaria | Amaranthus | Chenopodium | Viola |
|---|---|---|---|---|---|---|
| 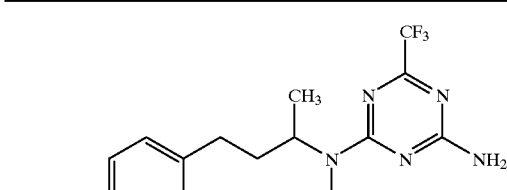 (16) | 500 | 90 | 100 | 100 | 100 | 100 |

TABLE B-continued
Post-emergence-test/greenhouse
| | | | | | | |
|---|---|---|---|---|---|---|
| 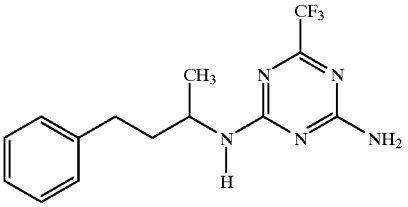 (14) | 500 | 70 | 100 | 100 | 100 | 100 |
| 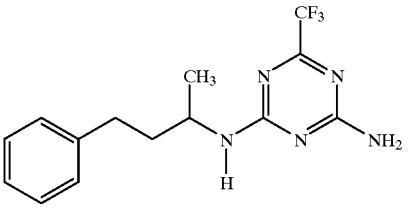 (67) | 1000 | 95 | 100 | 100 | 100 | 100 |
| Active compound of Preparation Ex. No | Application rate (g ai./ha) | Echinochloa | Amaranthus | Chenopodium | Viola |
|---|---|---|---|---|---|
| 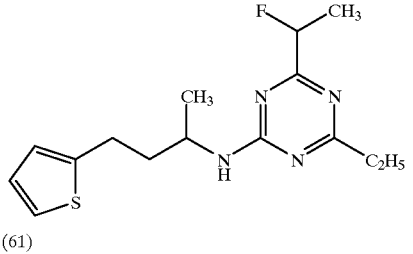 (61) | 500 | 100 | 100 | 100 | 100 |
| 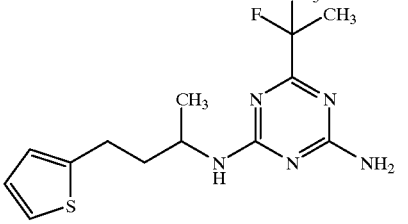 (62) | 500 | 100 | 100 | 100 | 100 |
| Active compound of Preparation Ex. No | Application rate (g ai./ha) | Avena fatua | Setaria | Abutilon | Amaranthus | Sinapis |
|---|---|---|---|---|---|---|
| 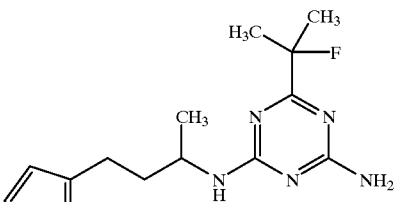 (63) | 1000 | 100 | 90 | 100 | 100 | 100 |

TABLE B-continued

Post-emergence-test/greenhouse

| Active compound of Preparation Ex. No | Application rate (g ai./ha) | Setaria | Abutilon | Amaranthus | Xanthium |
|---|---|---|---|---|---|
| 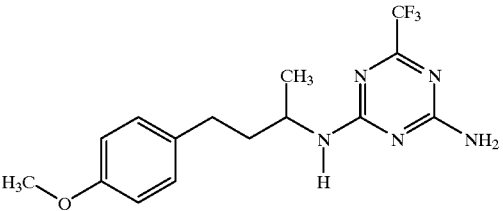 (18) | 1000 | 100 | 100 | 100 | 100 |

What is claimed is:

1. A substituted 2-amino-4-alkylamino-1,3,5-triazine of the formula (I),

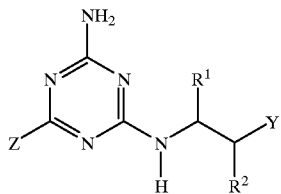

(I)

wherein $R^1$ represents methyl; or halogen-, cyano-, carboxyl-, carbamoyl-, thiocarbamoyl- or $C_1$–$C_4$-alkoxy-substituted methyl, $R^2$ represents hydrogen or $C_1$–$C_3$-alkyl, Y represents heterocyclylmethyl heterocyclyloxy; substituted heterocyclylmethyl; or substituted heterocyclyloxy;

wherein heterocyclyl is a member selected from the group consisting of furyl, benzofuryl, dihydrobenzofuryl, tetrahydrofuryl, thienyl, benzothienyl, thiazolyl, benzothiazolyl, oxazolyl, benzoxazolyl, thiadiazolyl, oxadiazolyl, pyrazolyl, pyrrolyl, indolyl, pyridinyl, quinolinyl, isoquinolinyl and pyrimidinyl; and wherein the substituents of the substituted heterocyclylmethyl and substituted heterocyclyloxy are each selected independently from the group consisting of hydroxyl; cyano; nitro; halogen; hydroxy-, cyano- or halogen-substituted $C_1$–$C_6$-alkyl or $C_1$–$C_6$-alkoxy; halogen-substituted $C_1$–$C_6$-alkylcarbonyl, $C_1$–$C_6$-alkoxycarbonyl, $C_1$–$C_6$-alkylthio, $C_1$–$C_6$-alkylsulphinyl or $C_1$–$C_6$-alkylsulphonyl; hydroxyl-, cyano-, nitro-, halogen-, $C_1$–$C_4$-alkyl-, $C_1$–$C_4$-halocenoalkyl-, $C_1$–$C_4$-alkoxy- or $C_1$–$C_4$-halogenoalkoxy-substituted phenyl or phenoxy; and halogen-substituted methylenedioxy or ethylenedioxy, and Z represents hydrogen; $C_1$–$C_6$-alkyl; $C_1$–$C_6$-alkylcarbonyl; $C_1$–$C_6$-alkoxycarbonyl; $C_1$–$C_6$-alkylsulphinyl; $C_1$–$C_6$-alkylsulphonyl; $C_2$–$C_6$-alkenyl; $C_2$–$C_6$-alkynyl; hydroxyl-, cyano-, nitro-, halogen-, $C_1$–$C_4$-alkoxy-, $C_1$–$C_4$-alkylcarbonyl-, $C_1$–$C_4$-alkoxycarbonyl-, $C_1$–$C_4$-alkylthio-, $C_1$–$C_4$-alkylsulphinyl- or $C_1$–$C_4$-alkylsulphonyl-substituted $C_1$–$C_6$-alkyl, $C_1$–$C_6$-alkylcarbonl, $C_1$–$C_6$-alkoxycarbonyl $C_1$–$C_6$-alkylsulphinyl or $C_1$–$C_6$-alkylsulphonyl; or halogen-substituted $C_2$–$C_6$-alkenyl or $C_2$–$C_6$-alkynyl.

2. The compound of claim 1, wherein $R^1$ represents methyl, fluorine substituted methyl or chlorine substituted methyl, $R^2$ represents hydrogen, methyl or ethyl, Y represents heterocyclylmethyl, heterocyclyloxy, substituted heterocyclylmethyl, or substituted heterocyclyloxy, wherein heterocyclyl is a member selected from the group consisting of furyl, benzofuryl, dihydrobenzofuryl, tetrahydrofuryl, thienyl, benzothienyl, thiazolyl, benzothiazolyl, oxazolyl, benzoxazolyl, thiadiazolyl, oxadiazolyl, pyrazolyl, pyrrolyl, indolyl, pyridinyl, quinolinyl, isoquinolinyl and pyrimidinyl; and wherein the substituents of the substituted heterocyclylmethyl and substituted heterocyclyloxy are each selected independently from the group consisting of hydroxy; cyano; nitro; fluorine; chlorine; bromine; hydroxyl- cyano-, fluorine- or chlorine-substituted methyl, ethyl, n- or i-propyl, n-, i-, s- or t-butyl, methoxy, ethoxy, n- or i-propoxy, or n-, i-, s- or t-butoxy; fluorine- or chlorine-substituted acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, or n- or i-propylsulphonyl; hydroxyl-, cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl or phenoxy; and fluorine- or chlorine-substituted methylenedioxy or ethylenedioxy, and Z represents hydrogen; hydroxyl-, cyano-, nitro-, fluorine-, chlorine-, methoxy-, ethoxy-, n- or i-propoxy-, n-, i-, s- or t-butoxy-, methylthio-ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methylsulphinyl, ethyl-sulphinyl, n- or i-propylsulphinyl, methylsulphonyl, ethylsulphonyl, or n- or i-propylsulphonyl; or fluorine-, chlorine- or bromine-substituted ethenyl, propenyl, butenyl, ethynyl, propynyl or butynyl.

3. A herbicidal composition comprising one or more compounds according to claim 1 and a member selected from the group consisting of an extender, a surfactant and mixtures thereof.

4. A method of controlling weeds comprising applying an effective amount of the herbicidal composition of claim 3 to said weeds or their habitat.

* * * * *